(12) United States Patent
Vind et al.

(10) Patent No.: US 7,671,175 B2
(45) Date of Patent: Mar. 2, 2010

(54) POLYPEPTIDES HAVING ANTIMICROBIAL ACTIVITY AND POLYNUCLEOTIDES ENCODING SAME

(75) Inventors: Jesper Vind, Vaerlose (DK); Dorotea Raventos Segura, Humlebaek (DK); Hans-Henrik Kristensen Hoegenhaug, Holte (DK); Per Holse Mygind, Soeborg (DK); Olivier Taboureau, Kgs. Lyngby (DK)

(73) Assignee: Novozymes Adenium Biotech A/S, Bagsvaerd (DK)

( * ) Notice: Subject to any disclaimer, the term of this patent is extended or adjusted under 35 U.S.C. 154(b) by 189 days.

(21) Appl. No.: 11/446,896

(22) Filed: Jun. 5, 2006

(65) Prior Publication Data
US 2007/0061923 A1    Mar. 15, 2007

Related U.S. Application Data

(60) Provisional application No. 60/688,589, filed on Jun. 8, 2005, provisional application No. 60/726,992, filed on Oct. 14, 2005.

(30) Foreign Application Priority Data

Jun. 6, 2005 (DK) ............................ 2005 00823
Oct. 13, 2005 (DK) ............................ 2005 01435

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)
*A61K 51/00* (2006.01)

(52) U.S. Cl. ..................... 530/324; 514/2; 424/1.69

(58) Field of Classification Search ............... 514/2
See application file for complete search history.

(56) References Cited

U.S. PATENT DOCUMENTS

2005/0124064 A1* 6/2005 Schnorr et al. ............. 435/386
2006/0211089 A1* 9/2006 Hoegenhaug et al. ...... 435/69.1
2006/0217306 A1* 9/2006 Kristensen et al. ........... 514/12

FOREIGN PATENT DOCUMENTS

WO    WO 03/044049        5/2003
WO    WO 03044049     *   5/2003

OTHER PUBLICATIONS

Mygind et al. Plectasin is a peptide antibiotic with therapeutic potential from a saprophytic fungus. (Novozymes) in Nature (London, (2005), 437(7061), 975-980.*

IP 12281D (Patent No.), Anon, Pseudoplectania antimicrobial peptide plectasin and gene, production with transgenic organisms of plectasin and its use in therapeutics, feed, and detergents; Cited At: IP.com Journal (2003), 3(5), 32 (No. IPCOM000012281D), Apr. 24, 2003).*

Mygind et al., Nature, vol. 437, pp. 975-980 (2005).

* cited by examiner

*Primary Examiner*—Maury Audet
(74) *Attorney, Agent, or Firm*—Elias Lambiris

(57) ABSTRACT

The present invention relates to isolated polypeptides having antimicrobial activity and isolated polynucleotides encoding the polypeptides. The invention also relates to nucleic acid constructs, vectors, and host cells comprising the polynucleotides as well as methods for producing and using the polypeptides.

35 Claims, No Drawings

POLYPEPTIDES HAVING ANTIMICROBIAL ACTIVITY AND POLYNUCLEOTIDES ENCODING SAME

CROSS-REFERENCE TO RELATED APPLICATIONS

This application claims priority or the benefit under 35 U.S.C. 119 of Danish application nos. PA 2005 00823 and PA 2005 01435 filed Jun. 6, 2005 and Oct. 13, 2005, respectively, and U.S. Provisional Application Nos. 60/688,589 and 60/726,992 filed Jun. 8, 2005 and Oct. 14, 2005, respectively, the contents of which are fully incorporated herein by reference.

FIELD OF THE INVENTION

The present invention relates to isolated polypeptides having antimicrobial activity and isolated polynucleotides encoding the polypeptides. The invention also relates to nucleic acid constructs, vectors, and host cells comprising the polynucleotides as well as methods for producing and using the polypeptides.

BACKGROUND OF THE INVENTION

It is an object of the present invention to provide polypeptides having improved antimicrobial activity. The polypeptides may exhibit reduced hemolytic activity and/or reduced cytotoxicity. The polypeptides may also exhibit reduced sensitivity towards cations, such as $Ca^{2+}$, $Mg^{2+}$, $Na^+$. The polypeptides may also exhibit a different antimicrobial spectrum compared to SEQ ID NO:1.

SUMMARY OF THE INVENTION

The present invention provides a polypeptide having antimicrobial activity which comprises, preferably consists of, an amino acid sequence which has at least 80% identity with amino acids 1 to 40 of the amino acid sequence:

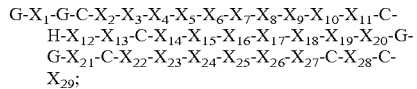

wherein
$X_1$=F, L, W or I; preferably $X_1$=F;
$X_2$=N, R, Q, V, G, S, A, K, L, M, D, H or Y; preferably $X_2$=N, R, Q, V, G, S, A, K or Y;
$X_3$=G, R, A or K; preferably $X_3$=G;
$X_4$=P, A, L, V, K or R; preferably $X_4$=P, K or R;
$X_5$=W or R;
$X_6$=D, A, G, K, L, T, N, F, H, M, P, Q, S, C, I, R, V or Y; preferably $X_6$=D, A, G, K, L, T, N, F, H, M, P, Q, S, V or Y;
$X_7$=E, G, A, L, C, Q or S; preferably $X_7$=E, G or S;
$X_8$=D, F, G, N, V, Y, H, K, L, P, S, T, W, I, M, A, C or R; preferably $X_8$=D, F, G, N, V, Y, H, K, L, P, S, T, W, I, M or R;
$X_9$=D or P; preferably $X_9$=D;
$X_{10}$=M, R, S, V, A, F, G, L, T, Y, W, E or K; preferably $X_{10}$=M, R, S, V, G, Y, L, F, T, W or K;
$X_{11}$=Q, R, L, F, G, H, S, A, C, I, K, M, P, T, V, W or Y; preferably $X_{11}$=Q, R, L, F, G, H, S, K or Y;
$X_{12}$=N, R, I, Y, V, K, T, Q, S, F, A, W, E or H;
$X_{13}$=H, A, F, Q, T, V or L; preferably $X_{13}$=H or L;
$X_{14}$=K, Q or R; preferably $X_{14}$=K or R;
$X_{15}$=S, A, V, N or F;
$X_{16}$=I, L, M, T, W or V; preferably $X_{16}$=I, L or V;
$X_{17}$=K, T or R;
$X_{18}$=G, H, K, A, P, F, I, Q, R, S, T, Y or N; preferably $X_{18}$=G, H, R, K or N;
$X_{19}$=Y, H, K, L, M, N, Q, S, V or R; preferably $X_{19}$=Y or R;
$X_{20}$=K, F, H, T, C or R; preferably $X_{20}$=K or R;
$X_{21}$=Y, F, R, A, H, L, M, S or W; preferably $X_{21}$=Y, F, R or W;
$X_{22}$=A, K, N, Q, T, E, H, I, R, S, V, G or Y; preferably $X_{22}$=A, K, N, Q, T, S or Y;
$X_{23}$=K, R or T; preferably $X_{23}$=K or R;
$X_{24}$=G, K, Q, E, N, S, T, A or R; preferably $X_{24}$=G, K, Q, A or R;
$X_{25}$=G, K, H, W or R; preferably $X_{25}$=G, K or R;
$X_{26}$=F, A, H, I, M, V, W, R or L; preferably $X_{26}$=F or L;
$X_{27}$=V, L, M, I, K, Q, R or T; preferably $X_{27}$=V, L, M or T;
$X_{28}$=K, H, N or R; preferably $X_{28}$=K or R;
$X_{29}$=Y, I, YRCG or YR; preferably $X_{29}$=Y or YR;

and which has less than 100% identity with amino acids 1 to 40 of SEQ ID NO:1.

The present invention also relates to nucleic acid constructs, recombinant expression vectors, and recombinant host cells comprising the polynucleotides.

The present invention also relates to methods for producing such polypeptides having antimicrobial activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the polypeptides of the invention.

DEFINITIONS

Antimicrobial activity: The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect and/or a virucidal effect, wherein the term "bactericidal" is to be understood as capable of killing bacterial cells. The term "bacteriostatic" is to be understood as capable of inhibiting bacterial growth, i.e. inhibiting growing bacterial cells. The term "fungicidal" is to be understood as capable of killing fungal cells. The term "fungistatic" is to be understood as capable of inhibiting fungal growth, i.e. inhibiting growing fungal cells. The term "virucidal" is to be understood as capable of inactivating virus. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

For purposes of the present invention, antimicrobial activity may be determined according to the procedure described by Lehrer et al., Journal of Immunological Methods, Vol. 137 (2) pp. 167-174 (1991). Alternatively, antimicrobial activity may be determined according to the NCCLS guidelines from CLSI (Clinical and Laboratory Standards Institute; formerly known as National Committee for Clinical and Laboratory Standards).

Polypeptides having antimicrobial activity may be capable of reducing the number of living cells of *Escherichia coli* (DSM 1576) to 1/100 after 24 hours (preferably after 12 hours, more preferably after 8 hours, more preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Escherichia coli* (DSM 1576) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

Polypeptides having antimicrobial activity may be capable of reducing the number of living cells of *Bacillus subtilis* (ATCC 6633) to 1/100 after 24 hours (preferably after 12 hours, more preferably after 8 hours, more preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the antimicrobial activity of the polypeptide consisting of the amino acid sequence shown as amino acids 1 to 40 of anyone of SEQ ID NO:3 to SEQ ID NO:225 or anyone of SEQ ID NO:226 to SEQ ID NO:251 or anyone of SEQ ID NO:252 to SEQ ID NO:274.

Defensin: The term "defensin" as used herein refers to polypeptides recognized by a person skilled in the art as belonging to the defensin class of antimicrobial peptides. To determine if a polypeptide is a defensin according to the invention, the amino acid sequence is preferably compared with the hidden markov model profiles (HMM profiles) of the PFAM database by using the freely available HMMER software package (see Example 7).

The PFAM defensin families include Defensin_1 or "Mammalian defensin" (accession no. PF00323), Defensin_2 or "Arthropod defensin" (accession no. PF01097), Defensin_beta or "Beta Defensin" (accession no. PF00711), Defensin_propep or "Defensin propeptide" (accession no. PF00879) and Gamma-thionin or "Gamma-thionins family" (accession no. PF00304).

The defensins may belong to the alpha-defensin class, the beta-defensin class, the theta-defensin class, the insect or arthropod defensin classes, or the plant defensin class.

In an embodiment, the amino acid sequence of a defensin according to the invention comprises 4, 5, 6, 7, or 8 cysteine residues, preferably 4, 5, or 6 cysteine residues, more preferably 4 or 6 cysteine residues, and most preferably 6 cysteine residues.

The defensins may also be synthetic defensins sharing the characteristic features of any of the defensin classes.

Examples of such defensins include, but are not limited to, α-Defensin HNP-1 (human neutrophil peptide) HNP-2 and HNP-3; β-Defensin-12, Drosomycin, Heliomicin, γ1-purothionin, Insect defensin A, and the defensins disclosed in PCT applications WO 99/53053, WO 02/06324, WO 02/085934, PCT/DK2005/000725, PCT/DK2005/000735 and PCT/DK2006/000155.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Variant: The term "variant" is defined herein as an antimicrobial polypeptide comprising one or more alterations, such as substitutions, insertions, deletions, and/or truncations of one or more specific amino acid residues at one or more specific positions in the polypeptide.

Numbering of Variants: In the present invention, a specific numbering of amino acid residue positions in the antimicrobial polypeptide variants is employed. For example, by aligning the amino acid sequences of known antimicrobial polypeptides, it is possible to designate an amino acid position number to any amino acid residue in any antimicrobial polypeptide.

Using the numbering system originating from the amino acid sequence of the antimicrobial polypeptide disclosed in SEQ ID NO:1, aligned with the amino acid sequence of a number of other antimicrobial polypeptides, it is possible to indicate the position of an amino acid residue in an antimicrobial polypeptide in regions of structural homology.

Multiple alignments of protein sequences may be made, for example, using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). Multiple alignments of DNA sequences may be done using the protein alignment as a template, replacing the amino acids with the corresponding codon from the DNA sequence.

Pairwise sequence comparison algorithms in common use are adequate to detect similarities between protein sequences that have not diverged beyond the point of approximately 20-30% sequence identity (Doolittle, 1992, *Protein Sci.* 1: 191-200; Brenner et al., 1998, *Proc. Natl. Acad. Sci. USA* 95, 6073-6078). However, truly homologous proteins with the same fold and similar biological function have often diverged to the point where traditional sequence-based comparison fails to detect their relationship (Lindahl and Elofsson, 2000, *J. Mol. Biol.* 295: 613-615). Greater sensitivity in sequence-based searching can be attained using search programs that utilize probabilistic representations of protein families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the protein of interest has one or more representatives in the protein structure databases. Programs such as GenTHREADER (Jones 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and salvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the protein of interest, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. These alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the various antimicrobial polypeptide variants of the present invention, the nomenclature described below is adapted for ease of reference. In all cases, the accepted IUPAC single letter or triple letter amino acid abbreviation is employed.

For an amino acid substitution, the following nomenclature is used: Original amino acid, position, substituted amino acid(s). Accordingly, the substitution of threonine with alanine at position 226 is designated as "T226A"; and substitution of tyrosine with tyrosine and arginine at position 40 (effectively adding arginine after tyrosine) is designated as "Y40YR". Multiple mutations are separated by addition marks ("+"), e.g., "G205R+S411F", representing mutations at positions 205 and 411 substituting glycine (G) with arginine (R), and serine (S) with phenylalanine (F), respectively.

Parent antimicrobial polypeptide: The term "parent" antimicrobial polypeptide as used herein means an antimicrobial polypeptide to which modifications, e.g., substitution(s), insertion(s), deletion(s), and/or truncation(s), are made to produce the antimicrobial polypeptide variants of the present invention. This term also refers to the polypeptide with which a variant is compared and aligned. The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. A parent may also be an allelic variant which is a polypeptide encoded by any of two or more alternative forms of a gene occupying the same chromosomal locus.

Identity: The relatedness between two amino acid sequences or between two nucleotide sequences is described by the parameter "identity".

For purposes of the present invention, the degree of identity between two amino acid sequences is determined by using the program FASTA included in version 2.0× of the FASTA program package (see W. R. Pearson and D. J. Lipman (1988), "Improved Tools for Biological Sequence Analysis", PNAS 85:2444-2448; and W. R. Pearson (1990) "Rapid and Sensitive Sequence Comparison with FASTP and FASTA", Methods in Enzymology 183:63-98). The scoring matrix used was BLOSUM50, gap penalty was −12, and gap extension penalty was −2.

The degree of identity between two nucleotide sequences is determined using the same algorithm and software package as described above. The scoring matrix used was the identity matrix, gap penalty was −16, and gap extension penalty was −4.

Alternatively, an alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5. The degree of identity between an amino acid sequence of the present invention (such as amino acids 1 to 40 of SEQ ID NO:1) and a different amino acid sequence is calculated as the number of exact matches in an alignment of the two sequences, divided by the length (number of amino acid residues) of the sequence of the present invention; or alternatively the output of Needle labeled "longest identity" is used as the percent identity and is calculated as follows: (Identical Residues×100)/(Length of Alignment−Number of Gaps in Alignment). The result is expressed in percent identity.

Polypeptide Fragment: The term "polypeptide fragment" is defined herein as a polypeptide having one or more amino acids deleted from the amino and/or carboxyl terminus of SEQ ID NO:2 or a homologous sequence thereof, wherein the fragment has antimicrobial activity.

Subsequence: The term "subsequence" is defined herein as a nucleotide sequence having one or more nucleotides deleted from the 5' and/or 3' end of SEQ ID NO:1 or a homologous sequence thereof, wherein the subsequence encodes a polypeptide fragment having antimicrobial activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of amino acids 1 to 40 of anyone of SEQ ID NO:2 to SEQ ID NO: 225 or anyone of SEQ ID NO:226 to SEQ ID NO:251 or anyone of SEQ ID NO:252 to SEQ ID NO:274 as well as genetic manipulation of the DNA encoding that polypeptide. The modification(s) can be substitution(s), deletion(s) and/or insertions(s) of the amino acid(s) as well as replacement(s) of amino acid side chain(s); or use of unnatural amino acids with similar characteristics in the amino acid sequence. In particular the modification(s) can be amidations, such as amidation of the C-terminus.

DETAILED DESCRIPTION OF THE INVENTION

Polypeptides Having Antimicrobial Activity

In a first aspect, the present invention provides a polypeptide having antimicrobial activity which comprises, preferably consists of, an amino acid sequence which has at least 70% identity (preferably at least 80% identity, more preferably at least 85% identity, even more preferably at least 90% identity, even more preferably at least 95% identity, most preferably 97% identity, and in particular 100% identity) with amino acids 1 to 40 of the amino acid sequence (I):

$$G-X_1-G-C-X_2-X_3-X_4-X_5-X_6-X_7-X_8-X_9-X_{10}-X_{11}-C-\\H-X_{12}-X_{13}-C-X_{14}-X_{15}-X_{16}-X_{17}-X_{18}-X_{19}-X_{20}-G-\\G-X_{21}-C-X_{22}-X_{23}-X_{24}-X_{25}-X_{26}-X_{27}-C-X_{28}-C-\\X_{29};$$

wherein $X_1$=F, L, W or I; preferably $X_1$=F;

$X_2$=N, R, Q, V, G, S, A, K, L, M, D, H or Y; preferably $X_2$=N, R, Q, V, G, S, A, K or Y; more preferably $X_2$=N, R, S or G;

$X_3$=G, R, A or K; preferably $X_3$=G;

$X_4$=P, A, L, V, K or R; preferably $X_4$=P, K or R;

$X_5$=W or R;

$X_6$=D, A, G, K, L, T, N, F, H, M, P, Q, S, C, I, R, V or Y; preferably $X_6$=D, A, G, K, L, T, N, F, H, M, P, Q, S, V or Y; more preferably $X_6$=D, S, A, G or N;

$X_7$=E, G, A, L, C, Q or S; preferably $X_7$=E, G or S;

$X_8$=D, F, G, N, V, Y, H, K, L, P, S, T, W, I, M, A, C or R; preferably $X_8$=D, F, G, N, V, Y, H, K, L, P, S, T, W, I, M or R; more preferably $X_8$=D, G or N;

$X_9$=D or P; preferably $X_9$=D;

$X_{10}$=M, R, S, V, A, F, G, L, T, Y, W, E or K; preferably $X_{10}$=M, R, S, V, G, Y, L, F, T, W or K; more preferably $X_{10}$=M, L, G or V;

$X_{11}$=Q, R, L, F, G, H, S, A, C, I, K, M, P, T, V, W or Y; preferably $X_{11}$=Q, R, L, F, G, H, S, K or Y; more preferably $X_{11}$=Q, K, R or F;

$X_{12}$=N, R, I, Y, V, K, T, Q, S, F, A, W, E or H; more preferably $X_{12}$=N, R, V or Q;

$X_{13}$=H, A, F, Q, T, V or L; preferably $X_{13}$=H or L;

$X_{14}$=K, Q or R; preferably $X_{14}$=K or R;

$X_{15}$=S, A, V, N or F;

$X_{16}$=I, L, M, T, W or V; preferably $X_{16}$=I, L or V;

$X_{17}$=K, T or R;

$X_{18}$=G, H, K, A, P, F, I, Q, R, S, T, Y or N; preferably $X_{18}$=G, H, R, K or N; more preferably $X_{18}$=G or R;

$X_{19}$=Y, H, K, L, M, N, Q, S, V or R; preferably $X_{19}$=Y or R;

$X_{20}$=K, F, H, T, C or R; preferably $X_{20}$=K or R;

$X_{21}$=Y, F, R, A, H, L, M, S or W; preferably $X_{21}$=Y, F, R or W;

$X_{22}$=A, K, N, Q, T, E, H, I, R, S, V, G or Y; preferably $X_{22}$=A, K, N, Q, T, S or Y; more preferably $X_{22}$=A, S or T;

$X_{23}$=K, R or T; preferably $X_{23}$=K or R;

$X_{24}$=G, K, Q, E, N, S, T, A or R; preferably $X_{24}$=G, K, Q, A or R; more preferably $X_{24}$=G or A;

$X_{25}$=G, K, H, W or R; preferably $X_{25}$=G, K or R;

$X_{26}$=F, A, H, I, M, V, W, R or L; preferably $X_{26}$=F or L;

$X_{27}$=V, L, M, I, K, Q, R or T; preferably $X_{27}$=V, L, M or T; more preferably $X_{27}$=V or L;

$X_{28}$=K, H, N or R; preferably $X_{28}$=K or R;

$X_{29}$=Y, I, YRCG or YR; preferably $X_{29}$=Y or YR;

and which has less than 100% identity with amino acids 1 to 40 of SEQ ID NO:1.

In an embodiment, the polypeptide of the invention is a polypeptide having antimicrobial activity which comprises, preferably consists of, an amino acid sequence which has at least 70% identity (preferably at least 80% identity, more preferably at least 85% identity, even more preferably at least 90% identity, even more preferably at least 95% identity, most preferably 97% identity, and in particular 100% identity) with amino acids 1 to 40 of the amino acid sequence (II):

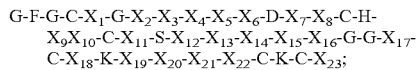

G-F-G-C-$X_1$-G-$X_2$-$X_3$-$X_4$-$X_5$-$X_6$-D-$X_7$-$X_8$-C-H-$X_9$$X_{10}$-C-$X_{11}$-S-$X_{12}$-$X_{13}$-$X_{14}$-$X_{15}$-$X_{16}$-G-G-$X_{17}$-C-$X_{18}$-K-$X_{19}$-$X_{20}$-$X_{21}$-$X_{22}$-C-K-C-$X_{23}$;

wherein $X_1$=N, R, Q, V, G, S, A, K or Y; preferably $X_1$=N, R, S or G;

$X_2$=P, K or R;

$X_3$=W or R;

$X_4$=D, A, G, K, L, T, N, F, H, M, P, Q, S, V or Y; preferably $X_4$=D, S, A, G or N;

$X_5$=E, G or S;

$X_6$=D, F, G, N, V, Y, H, K, L, P, S, T, W, I, M or R; preferably $X_6$=D, G or N;

$X_7$=M, R, S, V, G, Y, L, F, T, W or K; preferably $X_7$=M, L, G or V;

$X_8$=Q, R, L, F, G, H, S, K or Y; preferably $X_8$=Q, K, R or F;

$X_9$=N, R, I, Y, V, K, T, S, Q or H; preferably $X_9$=N, R, V or Q;

$X_{10}$=H or L;

$X_{11}$=K or R;

$X_{12}$=I, L or V;

$X_{13}$=K or R;

$X_{14}$=G, H, R, K or N; preferably $X_{14}$=G or R;

$X_{15}$=Y or R;

$X_{16}$=K or R;

$X_{17}$=Y, F, R or W;

$X_{18}$=A, K, N, Q, T, S or Y; preferably $X_{18}$=A, S or T;

$X_{19}$=G, K, Q, A or R; preferably $X_{19}$=G or A;

$X_{20}$=G, K or R;

$X_{21}$=F or L;

$X_{22}$=V, L, M or T; preferably $X_{22}$=V or L;

$X_{23}$=Y or YR;

and which has less than 100% identity with amino acids 1 to 40 of SEQ ID NO:1.

In another embodiment, the amino acid sequence (I) and/or (II) has 1, 2, 3, 4, 5, 6, 7 or 8 amino acid differences compared to the amino acid sequence of SEQ ID NO:1. Preferably 1, 2, 3, 4, 5 or 6; more preferably 1, 2, 3, 4 or 5; even more preferably 1, 2, 3 or 4; even more preferably 1, 2 or 3; and most preferably 1 or 2 amino acids are different compared to the amino acid sequence of SEQ ID NO:1.

In another embodiment, the amino acid sequence (I) and/or (II) has at least 60% identity with amino acids 1 to 40 of SEQ ID NO:1, preferably at least 65% identity, at least 70% identity, at least 75% identity, at least 80% identity, at least 85% identity, at least 90% identity, or at least 95% identity with amino acids 1 to 40 of SEQ ID NO:1.

In another embodiment, the amino acid sequence (I) and/or (II) has 0, 1, 2, 3, 4 or 5 insertions, preferably 0, 1, 2 or 3 insertions, more preferably 0, 1 or 2 insertions; and 0, 1, 2, 3, 4 or 5 deletions, preferably 0, 1, 2 or 3 deletions, more preferably 0, 1 or 2 deletions, as compared to SEQ ID NO:1 or anyone of SEQ ID NO:3 to SEQ ID NO:225 or anyone of SEQ ID NO:226 to SEQ ID NO:251 or anyone of SEQ ID NO:252 to SEQ ID NO:274.

In another embodiment, the polypeptide of the invention comprises, preferably consists of, an amino acid sequence which has at least 60% identity (preferably 70% identity, more preferably 80% identity, even more preferably 85% identity, even more preferably 90% identity, even more preferably 95% identity, and most preferably 100% identity) with amino acids 1 to 40 of anyone of SEQ ID NO:3 to SEQ ID NO:225 or anyone of SEQ ID NO:226 to SEQ ID NO:251 or anyone of SEQ ID NO:252 to SEQ ID NO:274, preferably anyone of SEQ ID NO:3 to SEQ ID NO:117 or anyone of SEQ ID NO:226 to SEQ ID NO:251 or anyone of SEQ ID NO:252 to SEQ ID NO:274.

The term "anyone of SEQ ID NO:3 to SEQ ID NO:117" is intended to mean SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, or SEQ ID NO:117.

The term "anyone of SEQ ID NO:118 to SEQ ID NO:225" is intended to mean anyone of SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, or SEQ ID NO:225.

The term "anyone of SEQ ID NO:226 to SEQ ID NO:251" is intended to mean anyone of SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, or SEQ ID NO:251.

The term "anyone of SEQ ID NO:252 to SEQ ID NO:274" is intended to mean anyone of SEQ ID NO:252, SEQ ID NO:253, SEQ ID NO:254, SEQ ID NO:255, SEQ ID NO:256, SEQ ID NO:257, SEQ ID NO:258, SEQ ID NO:259, SEQ ID NO:260, SEQ ID NO:261, SEQ ID NO:262, SEQ ID NO:263, SEQ ID NO:264, SEQ ID NO:265, SEQ ID NO:266, SEQ ID NO:267, SEQ ID NO:268, SEQ ID NO:269, SEQ ID NO:270, SEQ ID NO:271, SEQ ID NO:272, SEQ ID NO:273, or SEQ ID NO:274.

The term "anyone of SEQ ID NO:3 to SEQ ID NO:225" is intended to mean anyone of SEQ ID NO:3 to SEQ ID NO:117 or anyone of SEQ ID NO:118 to SEQ ID NO:225.

The term "anyone of SEQ ID NO:2 to SEQ ID NO:225" is intended to mean SEQ ID NO:2 or anyone of SEQ ID NO:3 to SEQ ID NO:225.

The amino acids making up the polypeptides of the invention may independently be selected from D or L forms. Preferably the polypeptide of the invention is a defensin polypeptide; more preferably an alpha defensin, a beta defensin, or an insect (arthropod) defensin.

The polypeptides of the invention may exhibit higher or at least equal, preferably higher, antimicrobial activity compared to the polypeptide of SEQ ID NO:1, determined as the Minimum Inhibitory Concentration (MIC), against *Staphylococcus carnosus* ATCC51365, *Staphylococcus aureus* ATCC29213 or *Staphylococcus aureus* ATCC25923 according to the NCCLS/CLSI guidelines, protocol M7-A6, vol. 20, No. 2: Methods for Dilution Antimicrobial Susceptibility Tests for Bacteria That Grow Aerobically.

In an embodiment, the present invention relates to artificial variants comprising a conservative substitution, deletion, and/or insertion of one or more amino acids of anyone of SEQ ID NO:2 to SEQ ID NO:225 or anyone of SEQ ID NO:226 to SEQ ID NO:251 or anyone of SEQ ID NO:252 to SEQ ID NO:274. Preferably, amino acid changes are of a minor nature, that is conservative amino acid substitutions or insertions that do not significantly affect the folding and/or activity of the protein; small deletions, typically of one to about 10 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., antimicrobial activity) to identify amino acid residues that are critical to the activity of the molecule. See also, Hilton et al., 1996, J. Biol. Chem. 271: 4699-4708. The biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 1 to 40 of anyone of SEQ ID NO:2 to SEQ ID NO:225 or anyone of SEQ ID NO:226 to SEQ ID NO:251 or anyone of SEQ ID NO:252 to SEQ ID NO:274 is 10, preferably 9, more preferably 8, more preferably 7, more preferably at most 6, more preferably at most 5, more preferably 4, even more preferably 3, most preferably 2, and even most preferably 1.

In another aspect, the present invention provides a variant of a parent antimicrobial polypeptide, which parent antimicrobial polypeptide has at least 60% identity with the amino acid sequence of SEQ ID NO:1, wherein the variant has antimicrobial activity and comprises a substitution in one or more positions, and wherein the substitutions are selected from:

F2L, F2W or F2I;
N5R, N5Q, N5V, N5G, N5S, N5A, N5K, N5L, N5M, N5D, N5H or N5Y;
G6R, G6A or G6K;
P7A, P7L, P7V, P7K or P7R;
W8R;
D9A, D9G, D9K, D9L, D9T, D9N, D9F, D9H, D9M, D9P, D9Q, D9S, D9C, D9I, D9R, D9V or D9Y;
E10G, E10A, E10L, E10C, E10Q or E10S;
D11F, D11G, D11N, D11V, D11Y, D11H, D11K, D11L, D11P, D11S, D11T, D11W, D11I, D11M, D11A, D11C or D11R;
D12P;
M13R, M13S, M13V, M13A, M13F, M13G, M13L, M13T, M13Y, M13W, M13E or M13K;
Q14R, Q14L, Q14F, Q14G, Q14H, Q14S, Q14A, Q14C, Q14I, Q14K, Q14M, Q14P, Q14T, Q14V, Q14W or Q14Y;
N17R, N17I, N17Y, N17V, N17K, N17T, N17S, N17Q, N17F, N17A, N17W, N17E or N17H; H18A, H18F, H18Q, H18T, H18V or H18L;
K20Q or K20R;
S21A, S21V, S21N or S21F;
I22L, I22M, I22T, I22W or I22V;
K23R or K23T;
G24H, G24K, G24A, G24P, G24F, G24I, G24Q, G24R, G24S, G24T, G24Y or G24N;
Y25H, Y25K, Y25L, Y25M, Y25N, Y25Q, Y25S, Y25V or Y25R;
K26F, K26H, K26T, K26C or K26R;
Y29F, Y29R, Y29A, Y29H, Y29L, Y29M, Y29S or Y29W;
A31K, A31N, A31Q, A31T, A31E, A31H, A31I, A31R, A31S, A31V, A31G or A31Y;
K32R or K32T;
G33K, G33Q, G33E, G33N, G33S, G33T, G33A or G33R;
G34K, G34H, G34W or G34R;
F35A, F35H, F35I, F35M, F35V, F35W, F35R or F35L;
V36L, V36M, V36I, V36K, V36Q, V36R or V36T;
K38H, K38N or K38R; and
Y40I, Y40YRCG or Y40YR.

Preferably the parent antimicrobial polypeptide has at least 70% identity, more preferably at least 80% identity, even more preferably at least 90% identity, and most preferably 95% identity with the amino acid sequence of SEQ ID NO:1. In particular the parent antimicrobial polypeptide may be identical to the amino acid sequence of SEQ ID NO:1.

In an embodiment the parent antimicrobial polypeptide is a defensin polypeptide; more preferably an alpha defensin, a beta defensin, or an insect (arthropod) defensin. Preferably the parent amino acid sequence exhibit antimicrobial activity.

In another embodiment, the parent antimicrobial polypeptide has 1, 2, 3, 4, 5, 6, 7 or 8 amino acid differences compared to the amino acid sequence of SEQ ID NO:1. Preferably 1, 2, 3, 4, 5 or 6; more preferably 1, 2, 3, 4 or 5; even more preferably 1, 2, 3 or 4; even more preferably 1, 2 or 3; and most preferably 1 or 2 amino acids are different compared to the amino acid sequence of SEQ ID NO:1.

N-Terminal Extension

An N-terminal extension of the polypeptides of the invention may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE and DD.

Kex2 Sites

Kex2 sites (see, e.g., Methods in Enzymology Vol 185, ed. D. Goeddel, Academic Press Inc. (1990), San Diego, Calif., "Gene Expression Technology") and kex2-like sites are di-basic recognition sites (i.e., cleavage sites) found between the pro-peptide encoding region and the mature region of some proteins.

Insertion of a kex2 site or a kex2-like site have in certain cases been shown to improve correct endopeptidase processing at the pro-peptide cleavage site resulting in increased protein secretion levels.

In the context of the invention insertion of a kex2 or kex2-like site result in the possibility to obtain cleavage at a certain position in the N-terminal extension resulting in an antimicrobial polypeptide being extended in comparison to amino acids 1 to 40 of anyone of SEQ ID NO:2 to SEQ ID NO:225 or anyone of SEQ ID NO:226 to SEQ ID NO:251 or anyone of SEQ ID NO:252 to SEQ ID NO:274.

Fused Polypeptides

The polypeptides of the present invention also include fused polypeptides or cleavable fusion polypeptides in which another polypeptide is fused at the N-terminus or the C-terminus of the polypeptide of the invention or a fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Sources of Polypeptides Having Antimicrobial Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may also be a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having antimicrobial activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to polynucleotides having a nucleotide sequence which encodes for a polypeptide of the invention. In particular, the present invention relates to polynucleotides consisting of a nucleotide sequence which encodes for a polypeptide of the invention. Due to the degeneracy of the genetic code, the skilled person will easily recognize that several nucleotide sequences encoding each of the polypeptides of the invention may be prepared. It is well known in the art which nucleotides make up codons encoding the amino acids of the polypeptides of the invention.

The present invention also relates to polynucleotides which encode fragments of the amino acid sequence shown as anyone of SEQ ID NO:2 to SEQ ID NO:225 or anyone of SEQ ID NO:226 to SEQ ID NO:251 or anyone of SEQ ID NO:252 to SEQ ID NO:274 that have antimicrobial activity. A subsequence of the polynucleotides is a nucleotide sequence wherein one or more nucleotides from the 5' and/or 3' end have been deleted.

The nucleotide sequence may be obtained by standard cloning procedures used in genetic engineering to relocate the nucleotide sequence from one location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated.

The nucleotide sequence may be of genomic, cDNA, RNA, semisynthetic, synthetic origin, or any combinations thereof.

Modification of a nucleotide sequence encoding a polypeptide of the present invention may be necessary for the synthesis of a polypeptide, which comprises an amino acid sequence that has at least one substitution, deletion and/or insertion as compared to amino acids 1 to 40 of anyone of SEQ ID NO:2 to SEQ ID NO:225 or anyone of SEQ ID NO:226 to SEQ ID NO:251 or anyone of SEQ ID NO:252 to SEQ ID NO:274. These artificial variants may differ in some engineered way from the polypeptide isolated from its native source, e.g., variants that differ in specific activity, thermostability, pH optimum, or the like.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for antimicrobial activity to identify amino acid residues that are critical to the activity of the molecule. Sites of interaction can also be determined by analysis of the three-dimensional structure as determined by such techniques as nuclear magnetic resonance analysis, crystallography or photoaffinity labelling (see, e.g., de Vos et al, 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the antimicrobial polypeptide.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces* cerevisiae glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GALL system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla *Ascomycota*, *Basidiomycota*, *Chytridiomycota*, and *Zygomycota* (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision *Eumycota* and *Oomycota* (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsisa*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, or *Ceriporiopsis subvermispora*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide.

The present invention also relates to methods for producing a polypeptide of the present invention, comprising (a) cultivating a host cell under conditions conducive for production of the polypeptide; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies. For example, an antimicrobial activity assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having antimicrobial activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162;

Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having antimicrobial activity of the present invention under conditions conducive for production of the polypeptide; and (b) recovering the polypeptide.

Compositions

The present invention also relates to compositions, such as pharmaceutical compositions, comprising a polypeptide of the present invention. Preferably, the compositions are enriched in such a polypeptide. The term "enriched" indicates that the antimicrobial activity of the composition has been increased, e.g., with an enrichment factor of 1.1.

The compositions may further comprise another pharmaceutically active agent, such as an additional biocidal or biostatic agent, such as another antimicrobial polypeptide exhibiting antimicrobial activity as defined above. The biocidal agent may be an antibiotic, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. The biocidal agent may also be an anti-mycotic agent, including polyenes, e.g. amphotericin B, nystatin; 5-flucosyn; and azoles, e.g. miconazol, ketoconazol, itraconazol and fluconazol.

In an embodiment the biocidal agent is a non-enzymatic chemical agent. In another embodiment the biocidal agent is a non-polypeptide chemical agent.

The compositions may comprise a suitable carrier material. The compositions may also comprise a suitable delivery vehicle capable of delivering the antimicrobial polypeptides of the invention to the desired locus when the compositions are used as a medicament.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Methods and Uses

The present invention is also directed to methods for using the polypeptides having antimicrobial activity. The antimicrobial polypeptides are typically useful at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, the present invention may also be used in all applications for which known antimicrobial compositions are useful, such as protection of wood, latex, adhesive, glue, paper, cardboard, textile, leather, plastics, caulking, and feed.

Other uses include preservation of foods, beverages, cosmetics such as lotions, creams, gels, ointments, soaps, shampoos, conditioners, antiperspirants, deodorants, mouth wash, contact lens products, enzyme formulations, or food ingredients.

Thus, the antimicrobial polypeptides of the invention may by useful as a disinfectant, e.g., in the treatment of infections in the eye or the mouth, skin infections; in antiperspirants or deodorants; for cleaning and disinfection of contact lenses and teeth (oral care).

In general it is contemplated that the antimicrobial polypeptides of the present invention are useful for cleaning, disinfecting or inhibiting microbial growth on any surface. Examples of surfaces, which may advantageously be contacted with the antimicrobial polypeptides of the invention are surfaces of process equipment used e.g. dairies, chemical or pharmaceutical process plants, water sanitation systems, oil processing plants, paper pulp processing plants, water treatment plants, and cooling towers. The antimicrobial polypeptides of the invention should be used in an amount, which is effective for cleaning, disinfecting or inhibiting microbial growth on the surface in question.

The antimicrobial polypeptides of the invention may additionally be used for cleaning surfaces and cooking utensils in food processing plants and in any area in which food is prepared or served such as hospitals, nursing homes and restaurants.

It may also be used as a preservation agent or a disinfection agent in water based paints.

The invention also relates to the use of an antimicrobial polypeptide or composition of the invention as a medicament. Further, an antimicrobial polypeptide or composition of the invention may also be used for the manufacture of a medicament for controlling or combating microorganisms, such as fungal organisms or bacteria, preferably gram positive bacteria.

The composition and antimicrobial polypeptide of the invention may be used as an antimicrobial veterinarian or human therapeutic or prophylactic agent. Thus, the composition and antimicrobial polypeptide of the invention may be used in the preparation of veterinarian or human therapeutic agents or prophylactic agents for the treatment of microbial infections, such as bacterial or fungal infections, preferably gram positive bacterial infections. In particular the microbial infections may be associated with lung diseases including, but not limited to, tuberculosis, pneumonia and cystic fibrosis; and sexual transmitted diseases including, but not limited to, gonorrhea and chlamydia.

The composition of the invention comprises an effective amount of the antimicrobial polypeptide of the invention.

The term "effective amount" when used herein is intended to mean an amount of the antimicrobial polypeptides of the invention, which is sufficient to inhibit growth of the microorganisms in question.

The invention also relates to wound healing compositions or products such as bandages, medical devices such as, e.g., catheters and further to anti-dandruff hair products, such as shampoos.

Formulations of the antimicrobial polypeptides of the invention are administered to a host suffering from or predisposed to a microbial infection. Administration may be topical, localized or systemic, depending on the specific microorganism, preferably it will be localized. Generally the dose of the antimicrobial polypeptides of the invention will be sufficient to decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use. The antimicrobial polypeptides of the invention are particularly useful for killing gram negative bacteria, including *Pseudomonas aeruginosa*, and *Chlamydia trachomatis*; and gram-positive bacteria, including streptococci such as *Streptococcus pneumonia, S. uberis, S. hyointestinalis, S. pyogenes* and *S. agalactiae*; and staphylococci such as *Staphylococcus aureus, S. epidermidis, S. simulans, S. xylosus* and *S. carnosus*.

Formulations of the antimicrobial polypeptides of the invention may be administered to a host suffering from or predisposed to a microbial lung infection, such as pneumonia; or to a microbial wound infection, such as a bacterial wound infection.

Formulations of the antimicrobial polypeptides of the invention may also be administered to a host suffering from or predisposed to a skin infection, such as acne, atopic dermatitis or seborrheic dermatitis; preferably the skin infection is a bacterial skin infection, e.g. caused by *Staphylococcus epidermidis, Staphylococcus aureus, Propionibacterium acnes, Pityrosporum ovale* or *Malassezia furfur*.

The antimicrobial polypeptides of the invention are also useful for in vitro formulations to kill microbes, particularly where one does not wish to introduce quantities of conventional antibiotics. For example, the antimicrobial polypeptides of the invention may be added to animal and/or human food preparations; or they may be included as an additive for in vitro cultures of cells, to prevent the overgrowth of microbes in tissue culture.

The susceptibility of a particular microbe to killing with the antimicrobial polypeptides of the invention may be determined by in vitro testing, as detailed in the experimental section.

Typically a culture of the microbe is combined with the antimicrobial polypeptide at varying concentrations for a period of time sufficient to allow the protein to act, usually between about one hour and one day. The viable microbes are then counted, and the level of killing determined.

Microbes of interest include, but are not limited to, Gram-negative bacteria, for example: *Citrobacter* sp.; *Enterobacter* sp.; *Escherichia* sp., e.g., *E. coli*; *Klebsiella* sp.; *Morganella* sp.; *Proteus* sp.; *Providencia* sp.; *Salmonella* sp., e.g,. *S. typhi, S. typhimurium*; *Serratia* sp.; *Shigella* sp.; *Pseudomonas* sp., e.g., *P. aeruginosa*; *Yersinia* sp., e.g., *Y. pestis, Y. pseudotuberculosis, Y. enterocolitica*; *Francicella* sp.; *Pasturella* sp.; *Vibrio* sp., e.g., *V. cholerae, V. parahemolyticus*; *Campylobacter* sp., e.g., *C. jejuni*; *Haemophilus* sp., e.g., *H. influenzae, H. ducreyi*; *Bordetella* sp., e.g., *B. pertussis, B. bronchiseptica, B. parapertussis*; *Brucella* sp., *Neisseria* sp., e.g., *N. gonorrhoeae, N. meningitidis*, etc. Other bacteria of interest include *Legionella* sp., e.g., *L. pneumophila*; *Listeria* sp., e.g., *L. monocytogenes*; *Mycoplasma* sp., e.g., *M. homi-nis, M. pneumoniae*; *Mycobacterium* sp., e.g., *M. tuberculosis, M. leprae*; *Treponema* sp., e.g., *T. pallidum*; *Borrelia* sp., e.g., *B. burgdorferi*; *Leptospirae* sp.; *Rickettsia* sp., e.g., *R. rickettsii, R. typhi*; *Chlamydia* sp., e.g., *C. trachomatis, C. pneumoniae, C. psittaci*; *Helicobacter* sp., e.g., *H. pylori*, etc.

Non-bacterial pathogens of interest include fungal and protozoan pathogens, e.g. *Plasmodia* sp., e.g., *P. falciparum, Trypanosoma* sp., e.g., *T. brucei*; shistosomes; *Entaemoeba* sp., *Cryptococcus* sp., *Candida* sp., e.g., *C. albicans*; etc.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific antimicrobial polypeptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The antimicrobial polypeptides of the invention may be systemic after administration or may be localized by the use of an implant or other formulation that acts to retain the active dose at the site of implantation.

In one embodiment, a formulation for topical use comprises a chelating agent that decreases the effective concentration of divalent cations, particularly calcium and magnesium. For example, agents such as citrate, EGTA or EDTA may be included, where citrate is preferred. The concentration of citrate will usually be from about 1 to 10 mM.

The compounds of the present invention can be administered alone, in combination with each other, or they can be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 pg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally neutral or acidic lipids, such as cholesterol, phosphatidyl serine, phosphatidyl glycerol, and the like.

For preparing the liposomes, the procedure described by Kato et al. (1991) *J. Biol. Chem.* 266:3361 may be used. Briefly, the lipids and lumen composition containing peptides are combined in an appropriate aqueous medium, conveniently a saline medium where the total solids will be in the range of about 1-10 weight percent. After intense agitation for short periods of time, from about 5-60 sec., the tube is placed in a warm water bath, from about 25-40+ C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Formulations with other Active Agents

For use in the subject methods, the antimicrobial polypeptides of the invention may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a formulation of the antimicrobial polypeptides of the invention, e.g. interferon gamma, tumor necrosis factor alpha, interleukin 12, etc.

In Vitro synthesis

The antimicrobial peptides of the invention may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein Animal Feed The present invention is also directed to methods for using the polypeptides having antimicrobial activity in animal feed, as well as to feed compositions and feed additives comprising the antimicrobial polypeptides of the invention.

The term animal includes all animals, including human beings. Examples of animals are non-ruminants, and ruminants, such as cows, sheep and horses. In a particular embodiment, the animal is a non-ruminant animal. Non-ruminant animals include mono-gastric animals, e.g. pigs or swine (including, but not limited to, piglets, growing pigs, and sows); poultry such as turkeys and chicken (including but not limited to broiler chicks, layers); young calves; and fish (including but not limited to salmon).

The term feed or feed composition means any compound, preparation, mixture, or composition suitable for, or intended for intake by an animal.

In the use according to the invention the antimicrobial polypeptide can be fed to the animal before, after, or simultaneously with the diet. The latter is preferred.

In a particular embodiment, the antimicrobial polypeptide, in the form in which it is added to the feed, or when being included in a feed additive, is well defined. Well-defined means that the antimicrobial polypeptide preparation is at least 50% pure as determined by Size-exclusion chromatography (see Example 12 of WO 01/58275). In other particular embodiments the antimicrobial polypeptide preparation is at least 60, 70, 80, 85, 88, 90, 92, 94, or at least 95% pure as determined by this method.

A well-defined antimicrobial polypeptide preparation is advantageous. For instance, it is much easier to dose correctly to the feed an antimicrobial polypeptide that is essentially free from interfering or contaminating other antimicrobial polypeptides. The term dose correctly refers in particular to the objective of obtaining consistent and constant results, and the capability of optimising dosage based upon the desired effect.

For the use in animal feed, however, the antimicrobial polypeptide need not be that pure; it may e.g. include other enzymes, in which case it could be termed an antimicrobial polypeptide preparation.

The antimicrobial polypeptide preparation can be (a) added directly to the feed (or used directly in a treatment process of vegetable proteins), or (b) it can be used in the production of one or more intermediate compositions such as feed additives or premixes that is subsequently added to the feed (or used in a treatment process). The degree of purity described above refers to the purity of the original antimicrobial polypeptide preparation, whether used according to (a) or (b) above.

Antimicrobial polypeptide preparations with purities of this order of magnitude are in particular obtainable using recombinant methods of production, whereas they are not so easily obtained and also subject to a much higher batch-to-batch variation when the antimicrobial polypeptide is produced by traditional fermentation methods.

Such antimicrobial polypeptide preparation may of course be mixed with other enzymes.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

The antimicrobial polypeptide can be added to the feed in any form, be it as a relatively pure antimicrobial polypeptide, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the antimicrobial polypeptide of the invention, the animal feed additives of the invention contain at least one fat soluble vitamin, and/or at least one water soluble vitamin, and/or at least one trace mineral, and/or at least one macro mineral.

Further, optional, feed-additive ingredients are colouring agents, aroma compounds, stabilisers, and/or at least one other enzyme selected from amongst phytases EC 3.1.3.8 or 3.1.3.26; xylanases EC 3.2.1.8; galactanases EC 3.2.1.89; and/or beta-glucanases EC 3.2.1.4.

In a particular embodiment these other enzymes are well defined (as defined above for antimicrobial polypeptide preparations).

Examples of other antimicrobial peptides (AMPs) are CAP18, Leucocin A, Tritrpticin, Protegrin-1, Thanatin, Defensin, Ovispirin such as Novispirin (Robert Lehrer, 2000), and variants, or fragments thereof which retain antimicrobial activity.

Examples of other antifungal polypeptides (AFPs) are the *Aspergillus giganteus*, and *Aspergillus niger* peptides, as well as variants and fragments thereof which retain antifungal activity, as disclosed in WO 94/01459 and WO 02/090384.

Usually fat and water soluble vitamins, as well as trace minerals form part of a so-called premix intended for addition to the feed, whereas macro minerals are usually separately added to the feed. Either of these composition types, when enriched with an antimicrobial polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat soluble vitamins are vitamin A, vitamin D3, vitamin E, and vitamin K, e.g. vitamin K3.

Examples of water soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium. The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one antimicrobial polypeptide as claimed herein.

Furthermore, or in the alternative (to the crude protein content indicated above), the animal feed composition of the invention has a content of metabolizable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolizable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samensteling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 5-30 mg enzyme protein per kg animal diet.

The antimicrobial polypeptide may be administered in one or more of the following amounts (dosage ranges): 0.01-200; or 0.01-100; or 0.05-100; or 0.05-50; or 0.10-10—all these ranges being in mg antimicrobial polypeptide protein per kg feed (ppm).

For determining mg antimicrobial polypeptide protein per kg feed, the antimicrobial polypeptide is purified from the feed composition, and the specific activity of the purified antimicrobial polypeptide is determined using a relevant assay (see under antimicrobial activity, substrates, and assays). The antimicrobial activity of the feed composition as such is also determined using the same assay, and on the basis of these two determinations, the dosage in mg antimicrobial polypeptide protein per kg feed is calculated.

The same principles apply for determining mg antimicrobial polypeptide protein in feed additives. Of course, if a sample is available of the antimicrobial polypeptide used for preparing the feed additive or the feed, the specific activity is determined from this sample (no need to purify the antimicrobial polypeptide from the feed composition or the additive).

The present invention is further described by the following examples which should not be construed as limiting the scope of the invention.

EXAMPLES

Chemicals used as buffers and substrates were commercial products of at least reagent grade.

Example 1

Evaluation of Minimal Effective Concentration

Three antimicrobial polypeptides, which are variants of SEQ ID NO:1, were tested for antimicrobial activity. A Minimal Effective Concentration assay (MEC, expressed as micrograms/mL) against different microorganisms was performed using the three plectasin mutants, Y40YR, N17R and Y25R following the protocol described in the book of Methods in Molecular Biology, Vol. 78, Antibacterial peptide protocol William M. Shafer, Human Press.

The plectasin mutant "Y40YR" was constructed by adding an arginine residue at the end of the plectasin amino acid sequence.

The results showed improved activity of all three antimicrobial peptides compared to wildtype plectasin (SEQ ID NO:1) against the bacteria Bacillus subtilis, Micrococcus luteus and Staphylococcus epidermidis.

TABLE 1

MEC values; all values are micrograms/mL

| Mutation | SEQ ID NO: | MEC against B. subtilis | MEC against M. luteus | MEC against S. epidermis |
|---|---|---|---|---|
| wildtype | 1 | 0.09 | 1.89 | 0.98 |
| Y40YR | 99 | 0.05 | 0.18 | 0.31 |
| N17R | 95 | 0.07 | 0.32 | 0.59 |
| Y25R | 117 | 0.04 | 1.40 | ND |

Example 2

Evaluation of Antimicrobial Activity

A range of antimicrobial polypeptides, which are variants of SEQ ID NO:1 (Plectasin), were tested for antimicrobial activity by expressing them in S. cerevisae and screening the supernatant of the yeast transformants for antimicrobial activity against Staphylococcus carnosus ATCC51365.

Growth media and solutions were prepared as described in Sambrook, Fritsch and Maniatis (1989), Molecular cloning, Cold Spring Harbour, Laboratory Press, New York.

Radial Diffusion Assay was carried out as described in Methods in Molecular Biology, 15 Vol. 78, Antibacterial peptide protocol, William M. Shafer, Human Press.

200-300 yeast transformant colonies were plated on 14 cm round plates containing 25 mL SC growth medium supplemented with 1.5% galactose, 0.5% glucose and 1.5% agarose. Plates were incubated for three hours at room temperature, overlaid with 25 mL of the same growth medium and allowed to grow for three days at 30 degrees Celsius.

Then the plates were overlaid with 25 mL of LB growth medium containing 1.5% agarose and $10^5$ cells of the indicator strain Staphylococcus carnosus and incubated at 30 degrees Celsius overnight to allow growth of the bacterial cells. Next day, the plates were stained with 1.5 mM MTT to facilitate visualization of the clearing zones.

Yeast colonies creating clearing zones were transferred to microtitter plates containing 200 micro-L of SC growth medium supplemented with 2% glucose and ampicillin (100 mg/L). Such plates designated "master plates" were incubated for 2 days at 30 degrees Celsius with shaking at 450 rpm to allow yeast growth.

10 micro-L SC growth medium from each well of the master plates were transferred to new microtitter plates containing 200 micro-L SC growth medium with 1.5% galactose and 0.5% glucose. These plates were called daughter plates and were incubated for 3 days at 30° C. under 450 rpm shaking to allow yeast growth and peptide synthesis.

Finally a Radial Diffusion Assay (RDA) was performed following the protocol described in Methods in Molecular Biology to analyse and quantify the antimicrobial activity of the yeast supernatants against S. carnosus.

Briefly, 30 mL of minimal underlay medium containing 1% agarose and $5 \times 10^5$ cfu/mL of S. carnosus was poured in an omnitray plate (Nunc, 242811). A Nunc TSP plate (#445497) was inserted immediately on the plate to allow a 96 well pattern formation. Once the media had solidified, the TSP plate was removed and 10 micro-L of yeast supernatant samples were applied on the holes. Plates were incubated 3 hours at 37 degrees Celsius and overlaid with 15 mL of LB agar growth medium. Finally, plates were incubated overnight at 37 degrees Celsius and coloured with 1.5 mM MTT to visualize the clearing zones.

Inspection and measurements of the clearing zones was performed on the plates. The corresponding yeast clones resulting in clearing zones of similar or increased size than the clones encoding for wild type plectasin were picked from the master plates and transferred to agar plates containing SC growth medium with 2% glucose and ampicillin (100 mg/L). Such plates were incubated for further 2 days at 30° C. to allow yeast growth. Subsequently, colony PCR was performed followed by sequence analysis to identify amino acid changes in the plectasin sequence.

The mutations and corresponding antimicrobial activities, relative to the activity of plectasin, are shown in Table 2. An activity of 2 corresponds to the activity of Plectasin. An activity of 3 is better than Plectasin, and 1 is worse than Plectasin.

TABLE 2

Antimicrobial activity data from the yeast screening assay

| Sequence | Mutation(s) | SEQ ID NO: | Activity |
|---|---|---|---|
| GFGCNGPWDEDDMQCHNHCKSIKGYKGGYCAKGGFVGKCY | wildtype | 1 | 2 |
| GFGCRGPWDEDDMQCHNHCKSIKGYKGGYCAKGGFVCKCY | N5R | 3 | 3 |
| GFGCQGPWDEDDMQCHNHCKSIKGYKGGYCAKGGFVCKCY | N5Q | 4 | 3 |
| GFGCVGPWDEDDMQCHNHCKSIKGYKGGYCAKGGFVCKCY | N5V | 5 | 3 |
| GFGCGGPWDEDDMQGHNHCKSTKGYKGGYCAKGGFVCKCY | N5G | 6 | 3 |
| GFGCSGPWDEDDMQCHNHCKSTKGYKGGYCAKGGFVCKCY | N5S | 7 | 3 |
| GFGCAGPWDEDDMQGHNHCKSIKGYKGGYCAKGGFVCKCY | N5A | 8 | 3 |
| GFGCNGKWDEDDMQCHNHGKSIKGYKGGYCAKGGFVCKCY | P7K | 9 | 3 |
| GFGCNGRWDEDDMQGHNHCKSIKGYKGGYCAKGGFVCKCY | P7R | 10 | 3 |
| GFGCNGPRDEDDMQCHNHCKSIKGYKGGYCAKGGPVCKCY | W8R | 11 | 3 |
| GFGCNGPWAEDDMQCHNHCKSIKGYKGGYCAKGGFVCKCY | D9A | 12 | 3 |
| GFGCNGPWGEDDMQCHNHCKSIKGYKGGYCAKGGFVCKCY | D9G | 13 | 3 |
| GFGCNGPWKEDDMQCHNHCKSIKGYKGGYCAKGGFVGKCY | D9K | 14 | 3 |
| GFGCNGPWLEDDMQCHNHCKSIKGYKGGYCAKGGPVCKCY | D9L | 15 | 3 |
| GFGCNGPWTEDDMQCHNHCKSIKGYKGGYCAKGGFVCKCY | D9T | 16 | 3 |
| GFGCNGPWYEDDMQCHNHCKSIKGYKGGYCAKGGFVCKCY | D9Y | 17 | 3 |
| GFGCNGPWFEDDMQCHNHCKSIKGYKGGYCAKGGFVCKCY | D9F | 18 | 3 |
| GFGCNGPWHEDDMQCHNHCKSTKGYKGGYAKGGFVCKCY | D9H | 19 | 3 |
| GFGCNGPWMEDDMQCHNHCKSTKGYKGGYCAKGGFVCKCY | D9M | 20 | 3 |
| GFGCNGPWNEDDMQCHNHCKSTKGYKGGYAKGGFVCKCY | D9N | 21 | 3 |
| GFGCNGPWPEDDMQCHNHGKSTKGYKGGYAKGGFVCKCY | D9P | 22 | 3 |
| GFGCNGPWQEDDMQCHNHCKSIKGYKGGYAKGGFVCKCY | D9Q | 23 | 3 |
| GFGCNGPWSEDDMQCHNHCKSIKGYKGGYAKGGFVCKCY | D9S | 24 | 3 |
| GFGCNGPWVEDDMQCHNHCKSIKGYKGGYCAKGGFVCKCY | D9V | 25 | 3 |
| GFGCNGPWDGDDMQCHNHCKSIKGYKGGYCAKGGFVCKCY | E10G | 26 | 3 |
| GFGCNGPWDSDDMQCHNHCKSIKGYKGGYCAKGGFVCKCY | E10S | 27 | 3 |
| GFGCNGPWDEFDMQCHNHCKSIKGYKGGYAKGGFVCKCY | D11F | 28 | 3 |
| GFGCNGPWDEGDMQCHNHCKSIKGYKGGYCAKGGFVCKCY | D11G | 29 | 3 |
| GFGCNGPWDEHDMQCHNHCKSIKGYKGGYCAKGGFVCKCY | D11H | 30 | 3 |
| GFGCNGPWDEKDMQCHNHCKSIKGYKGGYCAKGGFVCKCY | D11K | 31 | 3 |
| GFGCNGPWDELDMQCHNHCKSIKGYKGGYCAKGGFVCKCY | D11L | 32 | 3 |
| GFGCNGPWDEPDMQCHNHCKSIKGYKGGYCAKGGFVCKCY | D11P | 33 | 3 |
| GFGCNGPWDESDMQCHNHCKSIKGYKGGYCAKGGFVCKCY | D11S | 34 | 3 |
| GFGCNGPWDETDMQCHNHCKSIKGYKGGYCAKGGFVCKCY | D11T | 35 | 3 |
| GFGCNGPWDEVDMQCHNHCKSIKGYKGGYCAKGGFVCKCY | D11V | 36 | 3 |
| GFGCNGPWDEWDMQGHNHCKSIKGYKGGYAKGGFVCKCY | D11W | 37 | 3 |
| GFGCNGPWDEIDMQGHNHCKSIKGYKGGYCAKGGFVCKCY | D11I | 38 | 3 |

TABLE 2-continued

Antimicrobial activity data from the yeast screening assay

| Sequence | Mutation(s) | SEQ ID NO: | Activity |
|---|---|---|---|
| GFGCNGPWDEMDMQGHNHCKSIKGYKGGYCAKGGFVCKCY | D11M | 39 | 3 |
| GFGCNGPWDENDMQGHNHCKSIKGYKGGYCAKGGFVCKCY | D11N | 40 | 3 |
| GFGCNGPWDERDMQCHNHCKSIKGYKGGYCAKGGFVCKCY | D11R | 41 | 3 |
| GFGCNGPWDEYDMQCHNHCKSIKGYKGGYCAKGGFVCKCY | D11Y | 42 | 3 |
| GFGCNGPWDEDDRQCHNHCKSIKGYKGGYCAKGGFVCKCY | M13R | 43 | 3 |
| GFGCNGPWDEDDSQCHNHCKSIKGYKGGYCAKGGFVCKCY | M13S | 44 | 3 |
| GFGCNGPWDEDDVQCHNHCKSTKGYKGGYGAKGGFVCKCY | M13V | 45 | 3 |
| GFGCNGPWDEDDMFCHNHCKSIKGYKGGYGAKGGFVGKCY | Q14F | 46 | 3 |
| GFGCNGPWDEDDMGCHNHGKSIKGYKGGYCAKGGFVGKCY | Q14G | 47 | 3 |
| GFGCNGPWDEDDMHCHNHCKSIKGYKGGYCAKGGFVCKCY | Q14H | 48 | 3 |
| GFGCNGPWDEDDMSCHNHCKSIKGYKGGYCAKGGFVCKCY | Q14S | 49 | 3 |
| GFGCNGPWDEDDMYCHNHCKSIKGYKGGYCAKGGFVCKCY | Q14Y | 50 | 3 |
| GFGCNGPWDEDDMQCHNLCKSTKGYKGGYCAKGGFVCKCY | H18L | 51 | 3 |
| GFGCNGPWDEDDMQCHNHCKSLKGYKGGYCAKGGFVCKCY | I22L | 52 | 3 |
| GFGCNGPWDEDDMQCHNHCKSVKGYKGGYCAKGGFVCKCY | I22V | 53 | 3 |
| GFGCNGPWDEDDMQCHNHCKSIKHYKGGYCAKGGFVCKCY | G24H | 54 | 3 |
| GFGCNGPWDEDDMQCHNHCKSIKKYKGGYCAKGGFVCKCY | G24K | 55 | 3 |
| GFGCNGPWDEDDMQCHNHCKSIKNYKGGYCAKGGFVCKCY | G24N | 56 | 3 |
| GFGCNGPWDEDDMQCHNHCKSIKGYKGGFCAKGGFVCKCY | Y29F | 57 | 3 |
| GFGCNGPWDEDDMQCHNHCKSIKGYKGGRCAKGGFVCKCY | Y29R | 58 | 3 |
| GFGCNGPWDEDDMQCHNHCKSIKGYKGGWCAKGGFVCKCY | Y29W | 59 | 3 |
| GFGCNGPWDEDDMQCHNHCKSIKGYKGGYCKKGGFVCKCY | A31K | 60 | 3 |
| GFGCNGPWDEDDMQCHNHCKSIKGYKGGYCNKGGFVCKCY | A31N | 61 | 3 |
| GFGCNGPWDEDDMQCHNHCKSIKGYKGGYCQKGGFVCKCY | A31Q | 62 | 3 |
| GFGCNGPWDEDDMQCHNHCKSIKGYKGGYCTKGGFVCKCY | A31T | 63 | 3 |
| GFGCNGPWDEDDMQCHNHCKSIKGYKGGYCYKGGFVCKCY | A31Y | 64 | 3 |
| GFGCNGPWDEDDMQCHNHCKSIKGYKGGYCAKKGFVCKCY | G33K | 65 | 3 |
| GFGCNGPWDEDDMQCHNHCKSIKGYKGGYCAKQGFVCKCY | G33Q | 66 | 3 |
| GFGCNGPWDEDDMQCHNHCKSIKGYKGGYCAKRGFVCKCY | G33R | 67 | 3 |
| GFGCNGPWDEDDMQCHNHCKSIKGYKGGYCAKGKFVCKCY | G34K | 68 | 3 |
| GFGCNGPWDEDDMQCHNHCKSIKGYKGGYCAKGRFVCKCY | G34R | 69 | 3 |
| GFGCNGPWDEDDMQCHNHCKSIKGYKGGYCAKGGLVCKCY | F35L | 70 | 3 |
| GFGCNGPWDEDDMQCHNHCKSIKGYKGGYCAKGGFLCKCY | V36L | 71 | 3 |
| GFGCNGPWDEDDMQCHNHCKSIKGYKGGYCAKGGFMCKCY | V36M | 72 | 3 |
| GFGCNGPWDEDDMQCHNHCKSIKGYKGGYCAKGGFTCKCY | V36T | 73 | 3 |
| GFGCKGPWDEDDMQCHNHCKSIKGYRGGYCAKGGFVCKCY | N5K + K26R | 74 | 3 |

TABLE 2-continued

Antimicrobial activity data from the yeast screening assay

| Sequence | Mutation(s) | SEQ ID NO: | Activity |
|---|---|---|---|
| GFGCKGPWDEGDMQGHNHCKSIKGYKGGYCAKGGFVCKCY | N5K + D11G | 75 | 3 |
| GFGCSGPWDEDDMRCHNHCKAIRGYKGGYCAKGGFVCKCY | N5S + Q14R + S21A + K23R | 76 | 3 |
| GFGCSGPWDEDDMRCHSHGKSIRGYKGGYCAKGGFVCKCY | N5S + Q14R + N17S + K23R | 77 | 3 |
| GFGCNGPRDEDDRQCHNHCKSIKGYKGGYCAKGGFVCKCY | W8R + M13R | 78 | 3 |
| GFGCNGPWGEDDMRCHNHCKSIRGYKGGYCAKGGFVCKCY | D9G + Q14R + K23R | 79 | 3 |
| GFGCNGPWDGDDMRCHNHCKSIKGYKGGYCAKGGFVCKCY | E10G + Q14R | 80 | 3 |
| GFGCNGPWDEGDMQCHNHGKSIKGYKGGYCARGGFVCKCY | D11G + K32R | 81 | 3 |
| GFGCNGPWDEGDMQGHSHCKSIKGYKGGYCAKGGFVCKCY | D11G + N17S | 82 | 3 |
| GFGCNGPWDEGDMQCHNHCKSVKGYKGGYCAKGGFVCKCY | D11G + I22V | 83 | 3 |
| GFGCNGPWDENDMQCHNHCKSIKGYKGGYCAKGGFICKCY | D11N + V36I | 84 | 3 |
| GFGCNGPWDERDIQCHNHCKSIKGYKGGYCAKGGFVCKCY | D11R + M13I | 85 | 3 |
| GFGCNGPWDEDDMVCHNHCKSIKGYRGGYCAKGGFVCKCY | Q14V + K26R | 86 | 3 |
| GFGCNGPWDEDDMRCHNHCKSIKGYRGGYCAKGGPVCRCY | Q14R + K26R + K38R | 87 | 3 |
| GLGCNGPWDEDDMQCHNHCKSIKGYKGGYCAKGGFVCKCY | F2L | 118 | 2 |
| GWGCNGPWDEDDMQCHNHCKSIKGYKGGYCAKGGFVCKCY | F2W | 119 | 2 |
| GIGCNGPWDEDDMQCHNHCKSIKGYKGGYCAKGGFVCKCY | F2I | 120 | 2 |
| GFGCLGPWDEDDMQCHNHCKSIKGYKGGYCAKGGFVCKCY | N5L | 121 | 2 |
| GFGCMGPWDEDDMQCHNHCKSIKGYKGGYCAKGGPVGKCY | N5M | 122 | 2 |
| GFGCNRPWDEDDMQCHNHCKSIKGYKGGYCAKGGPVGKCY | G6R | 123 | 2 |
| GFGCNAPWDEDDMQCHNHCKSIKGYKGGYCAKGGPVGKCY | G6A | 124 | 2 |
| GFGCNKPWDEDDMQCHNHCKSIKGYKGGYCAKGGPVGKCY | G6K | 125 | 2 |
| GFGCNGAWDEDDMQCHNHCKSIKGYKGGYCAKGGPVGKCY | P7A | 126 | 2 |
| GFGCNGLWDEDDMQCHNHCKSIKGYKGGYCAKGGPVCKCY | P7L | 127 | 2 |
| GFGCNGVWDEDDMQCHNHCKSIKGYKGGYCAKGGPVCKCY | P7V | 128 | 2 |
| GFGCNGPWCEDDMQCHNHCKSIKGYKGGYCAKGGFVCKCY | D9C | 129 | 2 |
| GFGGNGPWIEDDMQCHNHCKSIKGYKGGYCAKGGFVCKCY | D9I | 130 | 2 |
| GFGCNGPWREDDMQCHNHCKSIKGYKGGYCAKGGFVCKCY | D9R | 131 | 2 |
| GFGCNGPWWEDDMQCHNHCKSIKGYKGGYCAKGGFVCKCY | D9W | 132 | 2 |
| GFGCNGPWDADDMQCHNHCKSIKGYKGGYCAKGGFVCKCY | E10A | 133 | 2 |
| GFGCNGPWDLDDMQCHNHCKSIKGYKGGYCAKGGPVCKCY | E10L | 134 | 2 |
| GFGCNGPWDCDDMQCHNHCKSIKGYKGGYCAKGGPVCKCY | E10C | 135 | 2 |
| GFGCNGPWDQDDMQCHNHCKSIKGYKGGYCAKGGPVCKCY | E10Q | 136 | 2 |
| GFGCNGPWDEADMQCHNHCKSIKGYKGGYCAKGGPVCKCY | D11A | 137 | 2 |
| GFGCNGPWDECDMQCHNHCKSIKGYKGGYCAKGGPVCKCY | D11C | 138 | 2 |
| GFGCNGPWDEDPMQCHNHCKSIKGYKGGYCAKGGPVCKCY | D12P | 139 | 2 |

TABLE 2-continued

Antimicrobial activity data from the yeast screening assay

| Sequence | Mutation(s) | SEQ ID NO: | Activity |
|---|---|---|---|
| GFGCNGPWDEDDAQCHNHCKSIKGYKGGYCAKGGPVCKCY | M13A | 140 | 2 |
| GFGCNGPWDEDDPQCHNHCKSIKGYKGGYCAKGGPVCKCY | M13F | 141 | 2 |
| GFGCNGPWDEDDGQCHNHCKSIKGYKGGYCAKGGFVCKCY | M13G | 142 | 2 |
| GFGCNGPWDEDDLQCHNHCKSIKGYKGGYAKGGFVCKCY | M13L | 143 | 2 |
| GFGCNGPWDEDDTQCHNHCKSIKGYKGGYCAKGGFVCKCY | M13T | 144 | 2 |
| GFGCNGPWDEDDYQCHNHCKSIKGYKGGYCAKGGFVCKCY | M13Y | 145 | 2 |
| GFGCNGPWDEDDMACHNHCKSIKGYKGGYCAKGGPVCKCY | Q14A | 146 | 2 |
| GFGCNGPWDEDDMCCHNHCKSIKGYKGGYCAKGGFVCKCY | Q14C | 147 | 2 |
| GFGCNGPWDEDDMICHNHCKSIKGYKGGYCAKGGPVCKCY | Q14I | 148 | 2 |
| GFGCNGPWDEDDMKCHNHCKSIKGYKGGYCAKGGFVCKCY | Q14K | 149 | 2 |
| GFGGNGPWDEDDMMCHNHCKSIKGYKGGYCAKGGFVCKCY | Q14M | 150 | 2 |
| GFGCNGPWDEDDMPCHNHCKSIKGYKGGYCAKGGFVCKCY | Q14P | 151 | 2 |
| GFGCNGPWDEDDMTCHNHCKSIKGYKGGYCAKGGFVCKCY | Q14T | 152 | 2 |
| GFGCNGPWDEDDMVCHNHCKSIKGYKGGYCAKGGFVCKCY | Q14V | 153 | 2 |
| GFGCNGPWDEDDMWGHNHCKSIKGYKGGYCAKGGFVGKCY | Q14W | 154 | 2 |
| GFGCNGPWDEDDMQCHNACKSTKGYKGGYCAKGGFVCKCY | H18A | 155 | 2 |
| GFGCNGPWDEDDMQCHNFCKSTKGYKGGYCAKGGFVCKCY | H18F | 156 | 2 |
| GFGCNGPWDEDDMQCHNQCKSIKGYKGGYCAKGGFVCKCY | H18Q | 157 | 2 |
| GFGCNGPWDEDDMQCHNTCKSIKGYKGGYCAKGGFVCKCY | H18T | 158 | 2 |
| GFGCNGPWDEDDMQCHNVCKSIKGYKGGYAKGGFVCKCY | H18V | 159 | 2 |
| GFGCNGPWDEDDMQCHNHCQSIKGYKGGYCAKGGFVCKCY | K20Q | 160 | 2 |
| GFGCNGPWDEDDMQCHNHCKSMKGYKGGYCAKGGFVCKCY | I22M | 161 | 2 |
| GFGGNGPWDEDDMQCHNHCKSTKGYKGGYCAKGGFVCKCY | I22T | 162 | 2 |
| GFGCNGPWDEDDMQCHNHCKSWKGYKGGYCAKGGFVCKCY | I22W | 163 | 2 |
| GFGCNGPWDEDDMQCHNHCKSIKAYKGGYCAKGGFVCKCY | G24A | 164 | 2 |
| GFGCNGPWDEDDMQCHNHGKSIKPYKGGYCAKGGFVCKCY | G24P | 165 | 2 |
| GFGCNGPWDEDDMQCHNHCKSIKFYKGGYCAKGGFVCKCY | G24F | 166 | 2 |
| GFGCNGPWDEDDMQCHNHCKSIKTYKGGYCAKGGFVCKCY | G24I | 167 | 2 |
| GFGCNGPWDEDDMQCHNHCKSIKQYKGGYCAKGGFVCKCY | G24Q | 168 | 2 |
| GFGCNGPWDEDDMQCHNHCKSIKRYKGGYCAKGGFVCKCY | G24R | 169 | 2 |
| GFGCNGPWDEDDMQCHNHCKSTKSYKGGYCAKGGFVCKCY | G24S | 170 | 2 |
| GFGCNGPWDEDDMQCHNHCKSTKTYKGGYCAKGGFVCKCY | G24T | 171 | 2 |
| GFGCNGPWDEDDMQCHNHCKSIKYYKGGYCAKGGFVCKCY | G24Y | 172 | 2 |
| GFGCNGPWDEDDMQCHNHCKSIKGHKGGYCAKGGFVCKCY | Y25H | 173 | 2 |
| GFGCNGPWDEDDMQCHNHCKSIKGKKGGYCAKGGFVCKCY | Y25K | 174 | 2 |
| GFGCNGPWDEDDMQCHNHCKSIKGLKGGYCAKGGFVCKCY | Y25L | 175 | 2 |

TABLE 2-continued

Antimicrobial activity data from the yeast screening assay

| Sequence | Mutation(s) | SEQ ID NO: | Activity |
|---|---|---|---|
| GFGCNGPWDEDDMQCHNHCKSIKGMKGGYCAKGGFVCKCY | Y25M | 176 | 2 |
| GFGCNGPWDEDDMQCHNHCKSIKGNKGGYCAKGGFVCKCY | Y25N | 177 | 2 |
| GFGCNGPWDEDDMQCHNHCKSIKGQKGGYCAKGGFVCKCY | Y25Q | 178 | 2 |
| GFGCNGPWDEDDMQCHNHCKSIKGSKGGYCAKGGFVCKCY | Y25S | 179 | 2 |
| GFGCNGPWDEDDMQCHNHCKSIKGVKGGYCAKGGFVCKCY | Y25V | 180 | 2 |
| GFGCNGPWDEDDMQCHNHCKSIKGYFGGYCAKGGFVCKCY | K26F | 181 | 2 |
| GFGCNGPWDEDDMQCHNHCKSIKGYHGGYCAKGGFVCKCY | K26H | 182 | 2 |
| GFGCNGPWDEDDMQCHNHCKSIKGYTGGYCAKGGFVCKCY | K26T | 183 | 2 |
| GFGCNGPWDEDDMQCHNHCKSIKGYKGGACAKGGFVCKCY | Y29A | 184 | 2 |
| GFGCNGPWDEDDMQCHNHCKSIKGYKGGHCAKGGFVCKCY | Y29H | 185 | 2 |
| GFGCNGPWDEDDMQCHNHCKSIKGYKGGLCAKGGFVCKCY | Y29L | 186 | 2 |
| GFGCNGPWDEDDMQCHNHCKSIKGYKGGMCAKGGFVCKCY | Y29M | 187 | 2 |
| GFGCNGPWDEDDMQCHNHCKSIKGYKGGSGAKGGFVCKCY | Y29S | 188 | 2 |
| GFGCNGPWDEDDMQCHNHCKSIKGYKGGYCEKGGFVCKCY | A31E | 189 | 2 |
| GFGCNGPWDEDDMQCHNHCKSIKGYKGGYCHKGGFVCKCY | A31H | 190 | 2 |
| GFGCNGPWDEDDMQCHNHCKSIKGYKGGYCIKGGFVCKCY | A31I | 191 | 2 |
| GFGCNGPWDEDDMQCHNHGKSIKGYKGGYCRKGGFVCKCY | A31R | 192 | 2 |
| GFGCNGPWDEDDMQCHNHCKSIKGYKGGYCSKGGFVCKCY | A31S | 193 | 2 |
| GFGCNGPWDEDDMQCHNHCKSIKGYKGGYCVKGGFVCKCY | A31V | 194 | 2 |
| GFGCNGPWDEDDMQCHNHGKSIKGYKGGYCARGGFVCKCY | K32R | 195 | 2 |
| GFGCNGPWDEDDMQCHNHGKSIKGYKGGYCATGGFVCKCY | K32T | 196 | 2 |
| GFGCNGPWDEDDMQCHNHCKSIKGYKGGYCAKEGFVCKCY | G33E | 197 | 2 |
| GFGCNGPWDEDDMQCHNHCKSIKGYKGGYCAKNGFVCKCY | G33N | 198 | 2 |
| GFGCNGPWDEDDMQCHNHCKSIKGYKGGYCAKSGFVCKCY | G33S | 199 | 2 |
| GFGCNGPWDEDDMQCHNHCKSIKGYKGGYCAKTGFVGKCY | G33T | 200 | 2 |
| GFGCNGPWDEDDMQCHNHCKSIKGYKGGYCAKGHFVGKCY | G34H | 201 | 2 |
| GFGCNGPWDEDDMQCHNHCKSIKGYKGGYCAKGWEVCKCY | G34W | 202 | 2 |
| GFGCNGPWDEDDMQCHNHCKSIKGYKGGYCAKGGAVCKCY | F35A | 203 | 2 |
| GFGCNGPWDEDDMQCHNHCKSIKGYKGGYCAKGGHVCKCY | F35H | 204 | 2 |
| GFGCNGPWDEDDMQCHNHCKSIKGYKGGYCAKGGTVCKCY | F35I | 205 | 2 |
| GFGCNGPWDEDDMQCHNHCKSIKGYKGGYCAKGGMVCKCY | F35M | 206 | 2 |
| GFGGNGPWDEDDMQCHNHCKSIKGYKGGYCAKGGVVCKCY | F35V | 207 | 2 |
| GFGCNGPWDEDDMQCHNHCKSIKGYKGGYCAKGGWVCKCY | F35W | 208 | 2 |
| GFGCNGPWDEDDMQCHNHCKSIKGYKGGYCAKGGFICKCY | V36I | 209 | 2 |
| GFGGNGPWDEDDMQCHNHCKSIKGYKGGYCAKGGFKCKCY | V36K | 210 | 2 |
| GFGCNGPWDEDDMQCHNHCKSIKGYKGGYCAKGGFQCKCY | V36Q | 211 | 2 |
| GFGCNGPWDEDDMQCHNHCKSIKGYKGGYCAKGGFRCKCY | V36R | 212 | 2 |

TABLE 2-continued

Antimicrobial activity data from the yeast screening assay

| Sequence | Mutation(s) | SEQ ID NO: | Activity |
|---|---|---|---|
| GFGCNGPWDEDDMQCHNHCKSIKGYKGGYCAKGGFVGHCY | K38H | 213 | 2 |
| GFGCNGPWDEDDMQCHNHCKSIKGYKGGYCAKGGFVCNCY | K38N | 214 | 2 |
| GFGCNGPWDEDDMQCHNHCKSIKGYKGGYCAKGGFVCRCY | K38R | 215 | 2 |
| GFGCNGPWDEDDMQCHNHCKSIKGYKGGYCAKGGFVCKCI | Y40I | 216 | 2 |
| GFGCNGPWLEDDMQCHNHCKSIKGYNGGYCAKGGFVCKCY | D9L + K26N | 217 | 2 |
| GFGCNGPWDELDIQCHNHCKSIKGYKGGYCAKGGFVCKCY | D11L + M13I | 218 | 2 |
| GFGCNGPWDEDDRQGHNHCKSIKGYKGGFCAKGGFVCKCY | M13R + Y29F | 219 | 2 |
| GFGCNGPWDEDDMRCHNHCKSIRGYRGGYCAKGGFVCKCY | Q14R + K23R + K26R | 220 | 2 |
| GFGCNGPWDEDDMRCHNHCRSIKGYKGGYCAKGGFVCKCY | Q14R + K20R | 221 | 2 |
| GFGCNGPWDEDDMSCHNHCKSIKGYKGGYCAKGGFVCRGY | Q14S + K38R | 222 | 2 |
| GFGGNGPWDEDDMQCHSHCKSIRGYKGGYCAKGGFVCKCY | N17S + K23R | 223 | 2 |
| GFGCNGPWDEDDMQCHNHCKSIKGYKGGFCARGGFVCKCY | Y29F + K32R | 224 | 2 |
| GFGGNGPWDEDDMQCHNHCKSIKGYKGGYCARGKFVCKGY | K32R + G34K | 225 | 2 |

Example 3

Identification of Antimicrobial Peptides with Improved Antimicrobial Activity

A range of antimicrobial polypeptides, which are variants of SEQ ID NO:1, were tested in the TAPS assay. TAPS may be used to identify new or improved genes encoding peptides that can kill or inhibit the growth of target cells (see PCT application WO 2004/033715). The TAPS assay, an acronym for Trans Acting Peptide System, is based on having a sensitive host producing a peptide followed by screening for its activity in trans against an indicator strain. The advantage of this system is based on that the antimicrobial peptide is expressed in the Gram-negative bacterium E. coli and its antimicrobial activity can be monitored on different microbes including Gram-negatives, positives or fungi. Additionally, TAPS offers the possibility to produce correctly folded AMPs containing disulfide bonds in the host cells, thereby retaining their antimicrobial activities.

The TAPS approach requires first, that expression of the peptide is under control of an inducible promoter with tight regulation, because the host cells are sensitive to the peptide when producing it. Secondly, the produced peptide has to be released to the media so that it can interact with the target organism.

The TAPS screening can be carried out either in solid or liquid media. On solid media, a plasmid library is initially introduced into E. coli host cells. It is important that the transformants are cultivated on the surface of a cellulose acetate filter placed on LB growth medium without inducer (arabinose) to avoid expression of the antimicrobial peptide and hence growth inhibition. In the next step, the filter containing the colonies is transferred to LB growth medium containing inducer (0.1% arabinose) to permit peptide synthesis. Subsequently, the target strain, for example S. carnosus, is overlaid onto the plate and allowed to grow for 12-16 hours at 37° C. Finally, visual inspection of the host cells capable of reducing the proliferation of the target cells is performed and the nucleotide sequence encoding for the antimicrobial peptide is recovered from the host cells. DNA sequence analysis of the variants is obtained to elucidate the nature of the peptide.

As mentioned above, the TAPS screening can also be performed using liquid medium. This procedure requires the use of robotics to analyze large number of clones. In this system, the host E. coli origami cells are transformed with the plasmid library and plated out on LB medium+0.2% glucose+ampicillin (200 mg/L). Independent colonies are then inoculated into 96 or 384-well plates containing 200 micro-L of TB medium +ampicillin (200 mg/L) and cultured overnight at 37 degrees Celsius. These cultures are then replicated robotically and grown to exponential phase until inducer (0.1% arabinose) is added to trigger peptide synthesis. The next step consists in hydrolyzing the cells such that the peptide is released to the media by hot acid hydrolysis. This treatment consists on adding 1 M sodium Phosphate buffer pH 2.3 to obtain a final pH approximately of 2.3 and incubating the cultures overnight at 80 degrees Celsius. Next day, a 25 micro-L aliquot of the hydrolyzed cultures is used to perform an activity test against the desired target organisms. The activity test performed was a Radial Diffusion Assay (RDA) where an aliquot of the hydrolyzed cultures was added to the agarose media inoculated with the target strain, S. carnosus. RDAs obtained from the screening plates containing clearing zones corresponding to clones exhibiting antimicrobial activity were easily identified. Measurements of the diameter of the clearing zones were performed to quantify the potency of the antimicrobial activity of the peptides.

The antimicrobial activity (against Staphylococcus carnosus) of the tested plectasin variants, which was measured using the TAPS assay, is shown in table 3. The antimicrobial activity corresponds to the clearing zone size and has been classified as 4>3>2>1; whereas 4 is better than 1, and wild-type activity corresponds to 1.

TABLE 3

Antimicrobial activity data from the TAPS assay

| Sequence | Mutation(s) | SEQ ID NO: | Activity |
|---|---|---|---|
|  | control |  | 0 |
| GFGCNGPWDEDDMQCHNHCKSTKGYKGGYCAKGGFVGKCY | wildtype | 1 | 1 |
| GFGCKGPWDEDDMQCHNHCKSIKGYKGGYCAKGGFVCKCY | N5K | 88 | 2 |
| GFGCYGPWDEDDMQCHNHCKSIKGYKGGYCAKGGFVCKCY | N5Y | 89 | 2 |
| GFGCNGPWDEDDKQCHNHCKSIKGYKGGYCAKGGFVCKCY | M13K | 90 | 3 |
| GFGCNGPWDEDDMLCHNHCKSIKGYKGGYCAKGGFVCKCY | Q14L | 91 | 4 |
| GFGCNGPWDEDDMRCHNHCKSIKGYKGGYCAKGGFVCKCY | Q14R | 92 | 4 |
| GFGCNGPWDEDDMQCHHHCKSIKGYKGGYCAKGGFVCKCY | N17H | 93 | 4 |
| GFGCNGPWDEDDMQCHIHCKSIKGYKGGYCAKGGFVGKCY | N17I | 94 | 2 |
| GFGCNGPWDEDDMQCHRHCKSIKGYKGGYCAKGGFVCKCY | N17R | 95 | 2 |
| GFGCNGPWDEDDMQGHYHCKSIKGYKGGYCAKGGFVCKCY | N17Y | 96 | 3 |
| GFGCNGPWDEDDMQCHNHCRSIKGYKGGYCAKGGFVCKCY | K20R | 97 | 2 |
| GFGCNGPWDEDDMQCHNHCKSIKGYRGGYCAKGGFVCKCY | K26R | 98 | 3 |
| GFGCNGPWDEDDMQGHNHCKSIKGYKGGYCAKGGFVCKCYR | Y40YR | 99 | 2 |
| GFGCYGPWDEDDMLCHNHCKSIKGYKGGYCAKGGFVCKCY | N5Y + Q14L | 100 | 2 |
| GFGGNGPWDEGDMQCHNHCKSIKGYRGGYCAKGGFVCKCY | D11G + K26R | 101 | 2 |
| GFGCNGPWDEGDKQCHNHCKSIKGYRGGYCAKGGFVCKCY | D11G + M13K + K26R | 102 | 3 |
| GFGCNGPWDEDDKQCHRHCKSIKGYKGGYCAKGGFVCKCYR | M13K + N17R + Y40YR | 103 | 3 |
| GFGCNGPWDEDDMQCHRHCKSIKGYKGGYCAKGGFVCKCYR | N17R + Y40YR | 104 | 3 |
| GFGCNGPWDENDMQCHNHCKFIKGYKGGYCAKGGFVCKCY | D11N + S21F | 105 | 4 |
| GFGCNGPWDEDDKQCHRHCKSIKGYKGGYCAKGGFVCKCY | M13K + N17R | 106 | 3 |
| GFGCNGPWDEDDKQCHNHCKSIKGYKGGYCAKGGFVCKCYR | M13K + Y40YR | 107 | 4 |
| GFGCNGPWDEDDKQCHNHCKSIKGYRGGYCAKGGFVCKCY | M13K + K26R | 108 | 4 |
| GFGCNGPWDEDDKQCHNHCKSIKGYKGGYCAKGGFVCRCY | M13K + K38R | 109 | 4 |
| GFGCNGPWDEGDMQCHNHCKSIKGYRGGYCAKGGFVCKCYR | D11G + K26R + Y40YR | 110 | 4 |
| GFGCNGPWDEGDKQCHNHCKSIKGYRGGYCAKGGFVCKCYR | D11G + M13K + K26R + Y40YR | 111 | 4 |
| GFGCNGPWDEDDMRCHNHCKSIKGYKGGYCAKGGFVCKCYR | Q14R + Y40YR | 112 | 3 |
| GFGCNGPWDEDDMRGHNHCKSIKGYKGGYCAKGGFICKCY | Q14R + V36I | 113 | 4 |
| GFGCNGPWDEDDMRCHNHCKSIKGYRGGYCAKGGFVCKCY | Q14R + K26R | 114 | 4 |
| GFGCNGPWDEDDMQCHNHCKFIKGYKGGYCTKGGFVCKCY | S21F + A31T | 115 | 2 |

Example 4

Evaluation of Antimicrobial Activity

Plectasin wild-type (SEQ ID NO:1) and five variants of Plectasin, which showed improved activity in the TAPS method and/or in the yeast system, were expressed and purified. The Minimal Inhibitory Concentration (MIC, micrograms/mL) was determined to test for their antimicrobial activity following the NCCLS guidelines (Clinical and Laboratory Standards Institute; formerly known as National Committee for Clinical and Laboratory Standards).

The results showed that all plectasin variants had improved activity, compared to wildtype plectasin, against *Stapylococcus aureus*, *Micrococcus luteus* and *Bacillus subtilis*.

TABLE 4

MIC values; all values are micrograms/mL

| Mutation(s) | SEQ ID NO: | MIC against S. aureus | MIC against M. luteus | MIC against B. subtilis |
|---|---|---|---|---|
| Wildtype | 1 | 8 | 32 | 1 |
| M13K + Y40YR | 107 | 2 | 2 | 0.25 |
| D11G + K26R | 101 | 2 | 8 | 0.50 |
| Q14K + K26R | 116 | 2 | 1 | 0.13 |
| D11G + K26R + Y40YR | 110 | 0.50 | 0.25 | 0.06 |
| D11G + M13K + K26R + Y40YR | 111 | 0.50 | 0.50 | <0.03 |

Example 5

Evaluation of Antimicrobial Activity

Plectasin wild-type (SEQ ID NO:1) and several variants of Plectasin were expressed and purified. The Minimal Inhibitory Concentration (MIC) was determined to test for their antimicrobial activity following the NCCLS guidelines from CLSI (Clinical and Laboratory Standards Institute; formerly known as National Committee for Clinical and Laboratory Standards).

The peptides were tested against the following strains:
A: *Staphylococcus aureus*, ATCC 29213;
B: *Staphylococcus aureus*, ATCC 25923;
C: *Staphylococcus aureus*, ATCC 29737;
D: *Staphylococcus aureus*, MRSA ST5 (2001), multi-resistant clinical human isolate from Statens Serum Institut, Denmark;
E: *Staphylococcus aureus*, MRSA ST80 (2003), multi-resistant clinical human isolate from Statens Serum Institut, Denmark.

All MIC values represent an average of two independent experiments; and all results in Table 5 are expressed relative to wildtype Plectasin:
0: >100% of Plectasin wildtype MIC;
1: 80-100% of Plectasin wildtype MIC;
2: 50-80% of Plectasin wildtype MIC;
3: <50% of Plectasin wildtype MIC.

TABLE 5

Relative MIC values; nd = not determined

| Mutation(s) | SEQ ID NO: | A | B | C | D | E |
|---|---|---|---|---|---|---|
| wildtype | 1 | 1 (8 μg/mL) | 1 (22 μg/mL) | 1 (4 μg/mL) | 1 (15 μg/mL) | 1 (22 μg/mL) |
| N5R + M13Y + N17R | 226 | 3 | 3 | 3 | 3 | 3 |
| D9S + Q14K + V36L | 227 | 3 | 3 | 3 | 3 | 3 |
| N5S + M13W + N17R | 228 | 3 | nd | 3 | 3 | 3 |
| Q14R + K26R + K38R | 87 | 3 | 3 | 3 | 3 | 3 |
| D9G + Q14R + K23R | 79 | 3 | 3 | 3 | 3 | 3 |
| M13G + N17R + G33A | 229 | 3 | 3 | 3 | 3 | 3 |
| N5S + D9S + M13L + Q14R + N17V + A31S | 230 | 3 | 3 | 3 | 3 | 3 |
| D9S + Q14L + K26R | 231 | 3 | 3 | 3 | 3 | 3 |
| N5S + D9A + K26R | 232 | 3 | 3 | 3 | 3 | 3 |
| Q14R + K20R | 221 | 3 | 3 | 3 | 3 | 3 |
| N5G + M13L | 233 | 2 | 3 | 3 | 3 | 3 |
| D9A + K38R | 234 | 3 | 3 | 3 | 3 | 3 |
| D11G + K32R | 81 | 1 | 3 | 3 | 2 | 3 |
| Q14F | 46 | 1 | nd | 3 | 2 | 3 |
| N5R + M13V | 235 | 3 | nd | 3 | 2 | 3 |
| N5G + M13Y + N17K | 236 | 3 | 3 | 3 | 3 | 2 |
| Q14K + K26R | 116 | 3 | 2 | 3 | 3 | 3 |
| M13F + Q14K + K26R | 237 | 3 | nd | 3 | 3 | 3 |
| M13K + K38R | 109 | 1 | 3 | 3 | 2 | 3 |

TABLE 5-continued

Relative MIC values; nd = not determined

| Mutation(s) | SEQ ID NO: | A | B | C | D | E |
|---|---|---|---|---|---|---|
| N5A + D9S + M13L + N17T | 238 | 0 | 3 | 3 | 2 | 3 |
| N17Y | 96 | 1 | 3 | 3 | 2 | 2 |
| M13T + Q14K + K26R | 239 | 1 | 3 | 3 | 2 | 0 |
| D9S | 24 | 2 | 3 | 3 | 2 | nd |
| N17R | 95 | nd | 3 | 3 | 3 | 2 |
| Q14R | 92 | 2 | 3 | 3 | 3 | 0 |
| N5S + Q14R + N17S + K23R | 77 | 1 | 3 | 3 | 3 | nd |
| N5R | 3 | 1 | 2 | 2 | 2 | 2 |
| D11G + K26R + Y40YR | 110 | 3 | 3 | 3 | 3 | nd |
| N5S + Q14R + S21A + K23R | 76 | 1 | 3 | 2 | 2 | 0 |
| M13L + Q14K + K26R | 240 | 3 | nd | 3 | 3 | nd |
| D9N + M13L + Q14R | 241 | 3 | 3 | 3 | 3 | 3 |
| D9A + Q14H + K26R + V36L | 242 | 3 | 3 | 3 | 3 | 3 |
| Q14R + K23R + K26R | 220 | 3 | 3 | 3 | 3 | 3 |
| N5S + D9S + M13V + N17R | 243 | 3 | 3 | 3 | 3 | 3 |
| N5G + D9S + M13L + N17Q + A31T | 244 | 3 | 3 | 3 | 3 | 3 |
| M13V + N17T | 245 | nd | 3 | 3 | 3 | 3 |
| D9S + M13L + Q14H | 246 | 3 | 3 | 3 | 3 | 3 |
| D9S + Q14L | 247 | 3 | nd | 3 | 3 | 3 |
| D9N + Q14H + K38R | 248 | 3 | 3 | 3 | 3 | 2 |
| M13Y + Q14K + K26R | 249 | 2 | 3 | 3 | 3 | 3 |
| D11N | 40 | 2 | 3 | 2 | 2 | 3 |
| N5S + D9S | 250 | 0 | 3 | 3 | 2 | 3 |
| G24R | 169 | 1 | 2 | nd | 2 | 2 |
| N5G + Q14K | 251 | 2 | 2 | 3 | 0 | 2 |
| N5K + K26R | 74 | 1 | 2 | 3 | 2 | 2 |

Example 6

Evaluation of Antimicrobial Activity

A large number of antimicrobial peptides of the invention were tested against a panel of 6 different strains of *Staphylococcus aureus* listed below:
*Staphylococcus aureus*, ATCC29213, MSSA, NCCLS reference strain;
*Staphylococcus aureus*, ATCC25923, MSSA, NCCLS reference strain;
*Staphylococcus aureus*, ATCC29737, MSSA;
*Staphylococcus aureus*, E33235, MSSA;
*Staphylococcus aureus*, 698-01, MRSA ST5, Str, Kan, Oxa;
*Staphylococcus aureus*, 566-03, MRSA ST80, Oxa, Tet, Fus, Kan.

*S. aureus* E33235, *S. aureus* 698-01 and *S. aureus* 566-03 are available from Statens Serum Institut, Denmark.

The staphylococci were exposed to the following peptide concentrations: 32; 16; 8; 4; 2; 1; 0.5; 0.25; 0.13; 0.6; and 0.03 microgram/mL. All peptides were purified, HPLC quantified and the concentrated peptides (>160 micrograms/mL) were diluted to 160 micrograms/mL in peptide dilution buffer (0.1% BSA, 0.01% Acetic Acid).

The MIC determination was done essentially as described by NCCLS/CLSI guidelines using caMHB. The MICs were read after 18-24 hours of 37° C. incubations and recorded along with the CFU in the table below.

A total number of 95 antimicrobial peptides of the invention were evaluated in duplicate against the 6 bacterial strains described above.

In the majority of the double determinations (93%), the MIC varied <2 fold. An average MIC is tabulated below. If the MIC was above 32 micrograms/mL, a value of 64 was used to calculate the average.

TABLE 6

Average MIC values

| Mutation(s) | SEQ ID NO: | Average MIC (micrograms/mL) |
|---|---|---|
| N5R + M13Y + N17R | 226 | 1 |
| D9N + M13L + Q14R | 241 | 1 |
| D9S + Q14K + V36L | 227 | 1 |
| D9A + Q14H + K26R + V36L | 242 | 1 |
| D9G + Q14R + K23R | 79 | 2 |
| Q14R + K23R + K26R | 220 | 2 |
| M13G + N17R + G33A | 229 | 2 |
| N5S + D9S + M13V + N17R | 243 | 2 |
| N5S + M13W + N17R | 228 | 2 |
| Q14R + K26R + K38R | 87 | 2 |
| N5S + D9S + M13L + Q14R + N17V + A31S | 230 | 2 |
| D9S + Q14L + K26R | 231 | 3 |
| N5S + D9A + K26R | 232 | 3 |
| N5G + D9S + M13L + N17Q + A31T | 244 | 3 |
| M13V + N17T | 245 | 3 |
| D9S + M13L + Q14H | 246 | 3

TABLE 6-continued

Average MIC values

| Mutation(s) | SEQ ID NO: | Average MIC (micrograms/mL) |
|---|---|---|
| N17I | 94 | 14 |
| N17S | 263 | 14 |
| N17S + K23R | 223 | 14 |
| N5G + D9A + Q14S + K23T + A31T | 264 | 14 |
| N17A | 265 | 15 |
| K2GR | 98 | 15 |
| M13S + Q14K + K26R | 266 | 15 |
| D11G + N17I | 267 | 16 |
| N5S + M13V + N17T | 268 | 16 |
| N5D + D9S + Q14R | 269 | 16 |
| D11G + I22V | 83 | 17 |
| S21A | 270 | 17 |
| N17R + Y25R | 271 | 18 |
| N5S + M13V + N17A | 272 | 18 |
| Q14G | 47 | 18 |
| D9G | 13 | 21 |
| N17T | 273 | 21 |
| Q14S | 49 | 21 |
| N5G | 6 | 24 |
| N5S | 7 | 24 |
| M13S | 44 | 24 |
| S21V | 274 | 26 |
| M13T | 144 | 26 |
| V36L | 71 | 26 |
| N5A | 8 | 29 |
| D9V | 25 | 30 |

Example 7

Using the HMM Files from the PFAM Database to Identify a Defensin

Sequence analysis using hidden markov model profiles (HMM profiles) may be carried out either online on the Internet or locally on a computer using the well-known HMMER freely available software package. The current version is HMMER 2.3.2 from October 2003.

The HMM profiles may be obtained from the well-known PFAM database. The current version is PFAM 16.0 from November 2004. Both HMMER and PFAM are available for all computer platforms from e.g. Washington University in St. Louis (USA), School of Medicine (http://pfam.wustl.edu and http://hmmer.wustl.edu).

If a query amino acid sequence, or a fragment thereof, belongs to one of the following five PFAM families, the amino acid sequence is a defensin according to the present invention:

Defensin_beta or "Beta Defensin", accession number: PF00711;

Defensin_propep or "Defensin propeptide", accession number: PF00879;

Defensin_1 or "Mammalian defensin", accession number: PF00323;

Defensin_2 or "Arthropod defensin", accession number: PF01097;

Gamma-thionin or "Gamma-thionins family", accession number: PF00304.

An amino acid sequence belongs to a PFAM family, according to the present invention, if it generates an E-value which is greater than 0.1, and a score which is larger or equal to zero, when the PFAM database is used online, or when the hmmpfam program (from the HMMER software package) is used locally.

When the sequence analysis is carried out locally using the hmmpfam program, it is necessary to obtain (download) the HMM profiles from the PFAM database. Two profiles exist for each family; xxx_ls.hmm for glocal searches, and xxx_fs.hmm for local searches ("xxx" is the name of the family). That makes a total of ten profiles for the five families mentioned above.

These ten profiles may be used individually, or joined (appended) into a single profile (using a text editor—the profiles are ASCII files) that could be named e.g. defensin-.hmm. A query amino acid sequence can then be evaluated by using the following command line:

hmmpfam-E 0.1 defensin.hmm sequence_file wherein "sequence file" is a file with the query amino acid sequence in any of the formats recognized by the HMMER software package.

If the score is larger or equal to zero (0.0), and the E-value is greater than 0.1, the query amino acid sequence is a defensin according to the present invention.

The PFAM database is further described in Bateman et al. (2004) "The Pfam Protein Families Database", Nucleic Acids Research, Vol. 32 (Database Issue) pp. D138-D141.

The invention claimed is:

1. A polypeptide having antimicrobial activity, which comprises the amino acid sequence of SEQ ID NO: 2:

Gly-Phe-Gly-Cys-Xaa-Gly-Pro-Trp-Xaa-Glu-Xaa-Asp-
                 5                  10
Xaa-Xaa-Cys-His-Xaa-His-Cys-Xaa-Ser-Ile-Xaa-Xaa-
       15                  20
Tyr-Xaa-Gly-Gly-Tyr-Cys-Xaa-Xaa-Xaa-Gly-Phe-Xaa-
25                  30                  35
Cys-Xaa-Cys-Tyr
       40 wherein
Xaa at position 5 is Ala, Arg, Asn, Asp, Gln, Gly, His, Leu, Lys, Met, Ser, Tyr or Val;
Xaa at position 9 is Ala, Arg, Asn, Asp, Cys, Gln, Gly, His, Ile, Leu, Lys, Met, Phe, Pro, Ser, Thr, Tyr or Val;
Xaa at position 11 is Ala, Arg, Asn, Asp, Cys, Gly, His, Ile, Leu, Lys, Met, Phe, Pro, Ser, Thr, Trp, Tyr or Val;
Xaa at position 13 is Ala, Arg, Glu, Gly, Leu, Lys, Met, Phe, Ser, Thr, Trp, Tyr or Val;
Xaa at position 14 is Ala, Arg, Cys, Gln, Gly, His, Ile, Leu, Lys, Met, Phe, Pro, Ser, Thr, Trp, Tyr or Val;
Xaa at position 17 is Ala, Arg, Asn, Gln, Glu, His, Ile, Lys, Phe, Ser, Thr, Trp, Tyr or Val;
Xaa at position 20 is Arg, Gln or Lys;
Xaa at position 23 is Arg, Lys or Thr;
Xaa at position 24 is Ala, Arg, Asn, Gln, Gly, His, Ile, Lys, Phe, Pro, Ser, Thr or Tyr;
Xaa at position 26 is Arg, Cys, His, Lys, Phe or Thr;
Xaa at position 31 is Ala, Arg, Asn, Gln, Glu, Gly, His, Ile, Lys, Ser, Thr, Tyr or Val;
Xaa at position 32 is Arg, Lys or Thr;
Xaa at position 33 is Ala, Arg, Asn, Gln, Glu, Gly, Lys, Ser or Thr;
Xaa at position 36 is Arg, Gln, Ile, Leu, Lys, Met, Thr or Val; and
Xaa at position 38 is Arg, Asn, His or Lys;
which has less than 100% identity with amino acids 1 to 40 of SEQ ID NO: 1.

2. The polypeptide of claim 1, wherein Xaa at position 5 is Ala, Arg, Asn, Gln, Gly, Lys, Ser, Tyr or Val.

3. The polypeptide of claim 1, wherein Xaa at position 5 is Arg, Asn, Gly or Ser.

4. The polypeptide of claim 1, wherein Xaa at position 9 is Ala, Asn, Asp, Gln, Gly, His, Leu, Lys, Met, Phe, Pro, Ser, Thr, Tyr or Val.

5. The polypeptide of claim 1, wherein Xaa at position 9 is Ala, Asn, Asp, Gly or Ser.

6. The polypeptide of claim 1, wherein Xaa at position 11 is Arg, Asn, Asp, Gly, His, Ile, Leu, Lys, Met, Phe, Pro, Ser, Thr, Trp, Tyr or Val.

7. The polypeptide of claim 1, wherein Xaa at position 11 is Asn, Asp or Gly.

8. The polypeptide of claim 1, wherein Xaa at position 13 is Arg, Gly, Leu, Lys, Met, Phe, Ser, Thr, Trp, Tyr or Val.

9. The polypeptide of claim 1, wherein Xaa at position 13 is Gly, Leu, Met, or Val.

10. The polypeptide of claim 1, wherein Xaa at position 14 is Arg, Gln, Gly, His, Leu, Lys, Phe, Ser or Tyr.

11. The polypeptide of claim 1, wherein Xaa at position 14 is Arg, Gln, Lys or Phe.

12. The polypeptide of claim 1, wherein Xaa at position 17 is Arg, Asn, Gln or Val.

13. The polypeptide of claim 1, wherein Xaa at position 20 is Arg or Lys.

14. The polypeptide of claim 1, wherein Xaa at position 24 is Arg, Asn, Gly, His or Lys.

15. The polypeptide of claim 1, wherein Xaa at position 24 is Arg or Gly.

16. The polypeptide of claim 1, wherein Xaa at position 26 is Arg or Lys.

17. The polypeptide of claim 1, wherein Xaa at position 31 is Ala, Asn, Gln, Lys, Ser, Thr or Tyr.

18. The polypeptide of claim 1, wherein Xaa at position 31 is Ala, Ser or Thr.

19. The polypeptide of claim 1, wherein Xaa at position 32 is Arg or Lys.

20. The polypeptide of claim 1, wherein Xaa at position 33 is Ala, Arg, Gln, Gly or Lys.

21. The polypeptide of claim 1, wherein Xaa at position 33 is Ala or Gly.

22. The polypeptide of claim 1, wherein Xaa at position 36 is Leu, Met, Thr or Val.

23. The polypeptide of claim 1, wherein Xaa at position 36 is Leu or Val.

24. The polypeptide of claim 1, wherein Xaa at position 38 is Arg or Lys.

25. The polypeptide of claim 1, which consists of the amino acid sequence of SEQ ID NO: 2.

26. The polypeptide of claim 1, which comprises the amino acid sequence of any of SEQ ID NOs: 3-10, 12-25, 28-50, 54-56, 60-67, 71-75, 77, 79, 81, 82, 84-104, 106-114, 116, 121, 122, 129-132, 137, 138, 140, 154, 160, 164-172, 181-183, 189-200, 209-215, 217, 218, 220-223, 226-240, 242-258, 260-269, 272, and 273.

27. The polypeptide of claim 1, which comprises the amino acid sequence of SEQ ID NO: 241.

28. An antimicrobial composition comprising the polypeptide of claim 1 and a pharmaceutically acceptable excipient.

29. The composition of claim 28, which further comprises an additional biocidal agent.

30. A detergent composition comprising a surfactant and the polypeptide of claim 1.

31. An animal feed additive comprising
(a) the polypeptide of claim 1; and
(b) a fat soluble vitamin, and/or
(c) a water soluble vitamin, and/or
(d) a trace mineral, and/or
(e) a macro mineral.

32. The animal feed additive of claim 31, which further comprises phytase, xylanase, galactanase, and/or beta-glucanase.

33. An animal feed composition having a crude protein content of 50 to 800 g/kg and comprising a polypeptide of claim 1.

34. A method for killing or inhibiting growth of microbial cells comprising contacting the microbial cells with the polypeptide of claim 1.

35. A method of treating a microbial infection, comprising administering to a human or animal the polypeptide of claim 1 in an amount effective to treat the microbial infection.

* * * * *

UNITED STATES PATENT AND TRADEMARK OFFICE
CERTIFICATE OF CORRECTION

PATENT NO. : 7,671,175 B2  Page 1 of 1
APPLICATION NO. : 11/446896
DATED : March 2, 2010
INVENTOR(S) : Vind et al.

It is certified that error appears in the above-identified patent and that said Letters Patent is hereby corrected as shown below:

In claim 1, column 196, line 42, delete "Gin" and insert -- Gln --.

In claim 1, column 196, line 44, delete "Gin" and insert -- Gln --.

In claim 1, column 196, line 46, delete "Gin" and insert -- Gln --.

In claim 1, column 196, line 53, delete "Gin" and insert -- Gln --.

In claim 1, column 196, line 55, delete "Gin" and insert -- Gln --.

Signed and Sealed this

Sixth Day of April, 2010

David J. Kappos
*Director of the United States Patent and Trademark Office*

SEQUENCE LISTING

<160> NUMBER OF SEQ ID NOS: 274

<210> SEQ ID NO 1
<211> LENGTH: 40
<212> TYPE: PRT
<213> ORGANISM: Pseudoplectania nigrella

```
<400> SEQUENCE: 1

Gly Phe Gly Cys Asn Gly Pro Trp Asp Glu Asp Met Gln Cys His
 1               5                  10                  15

Asn His Cys Lys Ser Ile Lys Gly Tyr Lys Gly Gly Tyr Cys Ala Lys
             20                  25                  30

Gly Gly Phe Val Cys Lys Cys Tyr
         35                  40

<210> SEQ ID NO 2
<211> LENGTH: 43
<212> TYPE: PRT
<213> ORGANISM: Artificial
<220> FEATURE:
<223> OTHER INFORMATION: Synthetic antimicrobial polypeptide
<220> FEATURE:
<221> NAME/KEY: MISC_FEATURE
<222> LOCATION: (2)..(2)
<223> OTHER INFORMATION: Xaa = Phe, Leu, Trp or Ile
<220> FEATURE:
<221> NAME/KEY: MISC_FEATURE
<222> LOCATION: (5)..(5)
<223> OTHER INFORMATION: Xaa = Asn, Arg, Gln, Val, Gly, Ser, Ala, Lys,
      Tyr, Leu, Asp, His or Met
<220> FEATURE:
<221> NAME/KEY: MISC_FEATURE
<222> LOCATION: (6)..(6)
<223> OTHER INFORMATION: Xaa = Gly, Arg, Ala or Lys
<220> FEATURE:
<221> NAME/KEY: MISC_FEATURE
<222> LOCATION: (7)..(7)
<223> OTHER INFORMATION: Xaa = Pro, Lys, Arg, Ala, Leu or Val
<220> FEATURE:
<221> NAME/KEY: MISC_FEATURE
<222> LOCATION: (8)..(8)
<223> OTHER INFORMATION: Xaa = Trp or Arg
<220> FEATURE:
<221> NAME/KEY: MISC_FEATURE
<222> LOCATION: (9)..(9)
<223> OTHER INFORMATION: Xaa = Asp, Ala, Gly, Lys, Leu, Thr, Asn, Phe,
      His, Met, Pro, Gln, Ser, Val, Tyr, Cys, Ile or Arg
<220> FEATURE:
<221> NAME/KEY: MISC_FEATURE
<222> LOCATION: (10)..(10)
<223> OTHER INFORMATION: Xaa = Glu, Gly, Ser, Ala, Leu, Cys or Gln
<220> FEATURE:
<221> NAME/KEY: MISC_FEATURE
<222> LOCATION: (11)..(11)
<223> OTHER INFORMATION: Xaa = Asp, Ala, Gly, Lys, Leu, Thr, Asn, Phe,
      His, Met, Pro, Gln, Ser, Val, Tyr, Ile, Cys, Arg, Trp or Met
<220> FEATURE:
<221> NAME/KEY: MISC_FEATURE
<222> LOCATION: (12)..(12)
<223> OTHER INFORMATION: Xaa = Asp or Pro
<220> FEATURE:
<221> NAME/KEY: MISC_FEATURE
<222> LOCATION: (13)..(13)
<223> OTHER INFORMATION: Xaa = Met, Arg, Ser, Val, Lys, Ala, Phe, Gly,
      Leu, Thr, Trp, Glu or Tyr
<220> FEATURE:
<221> NAME/KEY: MISC_FEATURE
<222> LOCATION: (14)..(14)
<223> OTHER INFORMATION: Xaa = Gln, Arg, Leu, Phe, Gly, His, Leu, Arg,
      Ser, Tyr, Ala, Cys, Ile, Lys, Met, Pro, Thr, Val or Trp
<220> FEATURE:
<221> NAME/KEY: MISC_FEATURE
<222> LOCATION: (17)..(17)
<223> OTHER INFORMATION: Xaa = Asn, Arg, Ile, Tyr, Val, Lys, Thr, Ser,
      Gln, Phe, Ala, Trp, Glu or His
<220> FEATURE:
<221> NAME/KEY: MISC_FEATURE
<222> LOCATION: (18)..(18)
<223> OTHER INFORMATION: Xaa = His, Leu, Ala, Phe, Gln, Thr or Val
<220> FEATURE:
<221> NAME/KEY: MISC_FEATURE
```

```
<222> LOCATION: (20)..(20)
<223> OTHER INFORMATION: Xaa = Lys, Arg or Gln
<220> FEATURE:
<221> NAME/KEY: MISC_FEATURE
<222> LOCATION: (21)..(21)
<223> OTHER INFORMATION: Xaa = Ser, Ala, Val, Asn or Phe
<220> FEATURE:
<221> NAME/KEY: MISC_FEATURE
<222> LOCATION: (22)..(22)
<223> OTHER INFORMATION: Xaa = Ile, Leu, Val, Met, Thr or Trp
<220> FEATURE:
<221> NAME/KEY: MISC_FEATURE
<222> LOCATION: (23)..(23)
<223> OTHER INFORMATION: Xaa = Lys, Thr or Arg
<220> FEATURE:
<221> NAME/KEY: MISC_FEATURE
<222> LOCATION: (24)..(24)
<223> OTHER INFORMATION: Xaa = Gly, His, Lys, Asn, Ala, Pro, Phe, Ile,
     Gln, Arg, Ser, Thr or Tyr
<220> FEATURE:
<221> NAME/KEY: MISC_FEATURE
<222> LOCATION: (25)..(25)
<223> OTHER INFORMATION: Xaa = Tyr, Arg, His, Lys, Leu, Met, Asn, Gln,
     Ser or Val
<220> FEATURE:
<221> NAME/KEY: MISC_FEATURE
<222> LOCATION: (26)..(26)
<223> OTHER INFORMATION: Xaa = Lys, Arg, Phe, His, Cys or Thr
<220> FEATURE:
<221> NAME/KEY: MISC_FEATURE
<222> LOCATION: (29)..(29)
<223> OTHER INFORMATION: Xaa = Tyr, Phe, Arg, Trp, Ala, His, Leu, Met or
     Ser
<220> FEATURE:
<221> NAME/KEY: MISC_FEATURE
<222> LOCATION: (31)..(31)
<223> OTHER INFORMATION: Xaa = Ala, Lys, Asn, Gln, Thr, Tyr, Glu, His,
     Ile, Arg, Ser, Gly or Val
<220> FEATURE:
<221> NAME/KEY: MISC_FEATURE
<222> LOCATION: (32)..(32)
<223> OTHER INFORMATION: Xaa = Lys, Arg or Thr
<220> FEATURE:
<221> NAME/KEY: MISC_FEATURE
<222> LOCATION: (33)..(33)
<223> OTHER INFORMATION: Xaa = Gly, Lys, Gln, Arg, Glu, Asn, Ser, Ala or
     Thr
<220> FEATURE:
<221> NAME/KEY: MISC_FEATURE
<222> LOCATION: (34)..(34)
<223> OTHER INFORMATION: Xaa = Gly, Lys, Arg, His, or Trp
<220> FEATURE:
<221> NAME/KEY: MISC_FEATURE
<222> LOCATION: (35)..(35)
<223> OTHER INFORMATION: Xaa = Phe, Leu, Ala, His, Ile, Met, Val, Arg or
     Trp
<220> FEATURE:
<221> NAME/KEY: MISC_FEATURE
<222> LOCATION: (36)..(36)
<223> OTHER INFORMATION: Xaa = Val, Leu, Met, Thr, Ile, Lys, Gln or Arg
<220> FEATURE:
<221> NAME/KEY: MISC_FEATURE
<222> LOCATION: (38)..(38)
<223> OTHER INFORMATION: Xaa = Lys, His, Asn or Arg
<220> FEATURE:
<221> NAME/KEY: MISC_FEATURE
<222> LOCATION: (40)..(40)
<223> OTHER INFORMATION: Xaa = Tyr or Ile
<220> FEATURE:
<221> NAME/KEY: MISC_FEATURE
<222> LOCATION: (41)..(41)
<223> OTHER INFORMATION: Xaa = Arg or is absent
<220> FEATURE:
<221> NAME/KEY: MISC_FEATURE
<222> LOCATION: (42)..(42)
<223> OTHER INFORMATION: Xaa = Cys or is absent
<220> FEATURE:
<221> NAME/KEY: MISC_FEATURE
<222> LOCATION: (43)..(43)
```

<223> OTHER INFORMATION: Xaa = Gly or is absent

<400> SEQUENCE: 2

```
Gly Xaa Gly Cys Xaa Xaa Xaa Xaa Xaa Xaa Xaa Xaa Xaa Cys His
1               5                   10                  15

Xaa Xaa Cys Xaa Xaa Xaa Xaa Xaa Gly Gly Xaa Cys Xaa Xaa
            20                  25                  30

Xaa Xaa Xaa Xaa Cys Xaa Cys Xaa Xaa Xaa Xaa
        35                  40
```

<210> SEQ ID NO 3
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 3

```
Gly Phe Gly Cys Arg Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 4
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 4

```
Gly Phe Gly Cys Gln Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 5
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 5

```
Gly Phe Gly Cys Val Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 6
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 6

-continued

```
Gly Phe Gly Cys Gly Gly Pro Trp Asp Glu Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 7
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 7

```
Gly Phe Gly Cys Ser Gly Pro Trp Asp Glu Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 8
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 8

```
Gly Phe Gly Cys Ala Gly Pro Trp Asp Glu Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 9
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 9

```
Gly Phe Gly Cys Asn Gly Lys Trp Asp Glu Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 10
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 10

```
Gly Phe Gly Cys Asn Gly Arg Trp Asp Glu Asp Met Gln Cys His
1               5                   10                  15
```

```
Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 11
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 11

Gly Phe Gly Cys Asn Gly Pro Arg Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 12
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 12

Gly Phe Gly Cys Asn Gly Pro Trp Ala Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 13
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 13

Gly Phe Gly Cys Asn Gly Pro Trp Gly Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 14
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 14

Gly Phe Gly Cys Asn Gly Pro Trp Lys Glu Asp Asp Met Gln Cys His
1               5                   10                  15

Asn His Cys Lys Ser Ile Lys Gly Tyr Lys Gly Gly Tyr Cys Ala Lys
            20                  25                  30
```

```
Gly Gly Phe Val Cys Lys Cys Tyr
        35                  40

<210> SEQ ID NO 15
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 15

Gly Phe Gly Cys Asn Gly Pro Trp Leu Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 16
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 16

Gly Phe Gly Cys Asn Gly Pro Trp Thr Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 17
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 17

Gly Phe Gly Cys Asn Gly Pro Trp Tyr Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 18
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 18

Gly Phe Gly Cys Asn Gly Pro Trp Phe Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 19
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 19

Gly Phe Gly Cys Asn Gly Pro Trp His Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 20
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 20

Gly Phe Gly Cys Asn Gly Pro Trp Met Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 21
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 21

Gly Phe Gly Cys Asn Gly Pro Trp Asn Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 22
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 22

Gly Phe Gly Cys Asn Gly Pro Trp Pro Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 23

<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 23

Gly Phe Gly Cys Asn Gly Pro Trp Gln Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 24
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 24

Gly Phe Gly Cys Asn Gly Pro Trp Ser Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 25
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 25

Gly Phe Gly Cys Asn Gly Pro Trp Val Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 26
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 26

Gly Phe Gly Cys Asn Gly Pro Trp Asp Gly Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 27
<211> LENGTH: 40
<212> TYPE: PRT
<213> ORGANISM: Artificial

-continued

```
<220> FEATURE:
<223> OTHER INFORMATION: Synthetic antimicrobial polypeptide

<400> SEQUENCE: 27

Gly Phe Gly Cys Asn Gly Pro Trp Asp Ser Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 28
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 28

Gly Phe Gly Cys Asn Gly Pro Trp Asp Glu Phe Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 29
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 29

Gly Phe Gly Cys Asn Gly Pro Trp Asp Glu Gly Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 30
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 30

Gly Phe Gly Cys Asn Gly Pro Trp Asp Glu His Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 31
<211> LENGTH: 40
<212> TYPE: PRT
<213> ORGANISM: Artificial
<220> FEATURE:
<223> OTHER INFORMATION: Synthetic antimicrobial polypeptide
```

-continued

```
<400> SEQUENCE: 31

Gly Phe Gly Cys Asn Gly Pro Trp Asp Glu Lys Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 32
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 32

Gly Phe Gly Cys Asn Gly Pro Trp Asp Glu Leu Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 33
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 33

Gly Phe Gly Cys Asn Gly Pro Trp Asp Glu Pro Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 34
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 34

Gly Phe Gly Cys Asn Gly Pro Trp Asp Glu Ser Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 35
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 35

Gly Phe Gly Cys Asn Gly Pro Trp Asp Glu Thr Asp Met Gln Cys His
```

-continued

```
                1               5                  10                  15
Asn His Cys Lys Ser Ile Lys Gly Tyr Lys Gly Gly Tyr Cys Ala Lys
                    20                  25                  30

Gly Gly Phe Val Cys Lys Cys Tyr
            35                  40

<210> SEQ ID NO 36
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 36

Gly Phe Gly Cys Asn Gly Pro Trp Asp Glu Val Asp Met Gln Cys His
1               5                   10                  15

Asn His Cys Lys Ser Ile Lys Gly Tyr Lys Gly Gly Tyr Cys Ala Lys
                    20                  25                  30

Gly Gly Phe Val Cys Lys Cys Tyr
            35                  40

<210> SEQ ID NO 37
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 37

Gly Phe Gly Cys Asn Gly Pro Trp Asp Glu Trp Asp Met Gln Cys His
1               5                   10                  15

Asn His Cys Lys Ser Ile Lys Gly Tyr Lys Gly Gly Tyr Cys Ala Lys
                    20                  25                  30

Gly Gly Phe Val Cys Lys Cys Tyr
            35                  40

<210> SEQ ID NO 38
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 38

Gly Phe Gly Cys Asn Gly Pro Trp Asp Glu Ile Asp Met Gln Cys His
1               5                   10                  15

Asn His Cys Lys Ser Ile Lys Gly Tyr Lys Gly Gly Tyr Cys Ala Lys
                    20                  25                  30

Gly Gly Phe Val Cys Lys Cys Tyr
            35                  40

<210> SEQ ID NO 39
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 39

Gly Phe Gly Cys Asn Gly Pro Trp Asp Glu Met Asp Met Gln Cys His
1               5                   10                  15

Asn His Cys Lys Ser Ile Lys Gly Tyr Lys Gly Gly Tyr Cys Ala Lys
```

Gly Gly Phe Val Cys Lys Cys Tyr
         35                  40

<210> SEQ ID NO 40
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 40

Gly Phe Gly Cys Asn Gly Pro Trp Asp Glu Asn Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
         35                  40

<210> SEQ ID NO 41
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 41

Gly Phe Gly Cys Asn Gly Pro Trp Asp Glu Arg Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
         35                  40

<210> SEQ ID NO 42
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 42

Gly Phe Gly Cys Asn Gly Pro Trp Asp Glu Tyr Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
         35                  40

<210> SEQ ID NO 43
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 43

Gly Phe Gly Cys Asn Gly Pro Trp Asp Glu Asp Asp Arg Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr

```
                35                  40

<210> SEQ ID NO 44
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 44

Gly Phe Gly Cys Asn Gly Pro Trp Asp Glu Asp Ser Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 45
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 45

Gly Phe Gly Cys Asn Gly Pro Trp Asp Glu Asp Val Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 46
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 46

Gly Phe Gly Cys Asn Gly Pro Trp Asp Glu Asp Met Phe Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 47
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 47

Gly Phe Gly Cys Asn Gly Pro Trp Asp Glu Asp Met Gly Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

```
<210> SEQ ID NO 48
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 48

Gly Phe Gly Cys Asn Gly Pro Trp Asp Glu Asp Asp Met His Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 49
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 49

Gly Phe Gly Cys Asn Gly Pro Trp Asp Glu Asp Asp Met Ser Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 50
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 50

Gly Phe Gly Cys Asn Gly Pro Trp Asp Glu Asp Asp Met Tyr Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 51
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 51

Gly Phe Gly Cys Asn Gly Pro Trp Asp Glu Asp Asp Met Gln Cys His
1               5                   10                  15

Asn Leu Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 52
<211> LENGTH: 40
<212> TYPE: PRT
```

<213> ORGANISM: Artificial
<220> FEATURE:
<223> OTHER INFORMATION: Synthetic antimicrobial polypeptide

<400> SEQUENCE: 52

Gly Phe Gly Cys Asn Gly Pro Trp Asp Glu Asp Asp Met Gln Cys His
1               5                   10                  15
Asn His Cys Lys Ser Leu Lys Gly Tyr Lys Gly Gly Tyr Cys Ala Lys
            20                  25                  30
Gly Gly Phe Val Cys Lys Cys Tyr
        35                  40

<210> SEQ ID NO 53
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 53

Gly Phe Gly Cys Asn Gly Pro Trp Asp Glu Asp Asp Met Gln Cys His
1               5                   10                  15
Asn His Cys Lys Ser Val Lys Gly Tyr Lys Gly Gly Tyr Cys Ala Lys
            20                  25                  30
Gly Gly Phe Val Cys Lys Cys Tyr
        35                  40

<210> SEQ ID NO 54
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 54

Gly Phe Gly Cys Asn Gly Pro Trp Asp Glu Asp Asp Met Gln Cys His
1               5                   10                  15
Asn His Cys Lys Ser Ile Lys His Tyr Lys Gly Gly Tyr Cys Ala Lys
            20                  25                  30
Gly Gly Phe Val Cys Lys Cys Tyr
        35                  40

<210> SEQ ID NO 55
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 55

Gly Phe Gly Cys Asn Gly Pro Trp Asp Glu Asp Asp Met Gln Cys His
1               5                   10                  15
Asn His Cys Lys Ser Ile Lys Lys Tyr Lys Gly Gly Tyr Cys Ala Lys
            20                  25                  30
Gly Gly Phe Val Cys Lys Cys Tyr
        35                  40

<210> SEQ ID NO 56
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 56

Gly Phe Gly Cys Asn Gly Pro Trp Asp Glu Asp Asp Met Gln Cys His
1               5                   10                  15

Asn His Cys Lys Ser Ile Lys Asn Tyr Lys Gly Gly Tyr Cys Ala Lys
            20                  25                  30

Gly Gly Phe Val Cys Lys Cys Tyr
        35                  40

<210> SEQ ID NO 57
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 57

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Phe Cys Ala Lys
            20                  25                  30

Gly Gly Phe Val Cys Lys Cys Tyr
        35                  40

<210> SEQ ID NO 58
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 58

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Arg Cys Ala Lys
            20                  25                  30

Gly Gly Phe Val Cys Lys Cys Tyr
        35                  40

<210> SEQ ID NO 59
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 59

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Trp Cys Ala Lys
            20                  25                  30

Gly Gly Phe Val Cys Lys Cys Tyr
        35                  40

<210> SEQ ID NO 60
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 60

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Lys Lys
                20                  25                  30

Gly Gly Phe Val Cys Lys Cys Tyr
            35                  40

<210> SEQ ID NO 61
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 61

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Asn Lys
                20                  25                  30

Gly Gly Phe Val Cys Lys Cys Tyr
            35                  40

<210> SEQ ID NO 62
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 62

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Gln Lys
                20                  25                  30

Gly Gly Phe Val Cys Lys Cys Tyr
            35                  40

<210> SEQ ID NO 63
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 63

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Thr Lys
                20                  25                  30

Gly Gly Phe Val Cys Lys Cys Tyr
            35                  40

<210> SEQ ID NO 64
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 64

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Tyr Lys
            20                  25                  30

Gly Gly Phe Val Cys Lys Cys Tyr
            35                  40

<210> SEQ ID NO 65
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 65

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Lys Gly Phe Val Cys Lys Cys Tyr
            35                  40

<210> SEQ ID NO 66
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 66

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gln Gly Phe Val Cys Lys Cys Tyr
            35                  40

<210> SEQ ID NO 67
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 67

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Arg Gly Phe Val Cys Lys Cys Tyr
            35                  40

<210> SEQ ID NO 68
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 68

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Lys Phe Val Cys Lys Cys Tyr
        35                  40

<210> SEQ ID NO 69
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 69

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Arg Phe Val Cys Lys Cys Tyr
        35                  40

<210> SEQ ID NO 70
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 70

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Leu Val Cys Lys Cys Tyr
        35                  40

<210> SEQ ID NO 71
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 71

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Leu Cys Lys Cys Tyr
        35                  40

<210> SEQ ID NO 72
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 72

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Met Cys Lys Cys Tyr
        35                  40

<210> SEQ ID NO 73
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 73

Gly Phe Gly Cys Asn Gly Pro Trp Asp Glu Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Thr Cys Lys Cys Tyr
        35                  40

<210> SEQ ID NO 74
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 74

Gly Phe Gly Cys Lys Gly Pro Trp Asp Glu Asp Met Gln Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 75
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 75

Gly Phe Gly Cys Lys Gly Pro Trp Asp Glu Gly Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 76
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 76

Gly Phe Gly Cys Ser Gly Pro Trp Asp Glu Asp Met Arg Cys His
1               5                   10                  15

Asn His Cys Lys Ala Ile Arg Gly Tyr Lys Gly Gly Tyr Cys Ala Lys
            20                  25                  30

Gly Gly Phe Val Cys Lys Cys Tyr
        35                  40

<210> SEQ ID NO 77
<211> LENGTH: 40

```
<212> TYPE: PRT
<213> ORGANISM: Artificial
<220> FEATURE:
<223> OTHER INFORMATION: Synthetic antimicrobial polypeptide

<400> SEQUENCE: 77

Gly Phe Gly Cys Ser Gly Pro Trp Asp Glu Asp Asp Met Arg Cys His
1               5                   10                  15

Ser His Cys Lys Ser Ile Arg Gly Tyr Lys Gly Gly Tyr Cys Ala Lys
            20                  25                  30

Gly Gly Phe Val Cys Lys Cys Tyr
        35                  40

<210> SEQ ID NO 78
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 78

Gly Phe Gly Cys Asn Gly Pro Arg Asp Glu Asp Asp Arg Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 79
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 79

Gly Phe Gly Cys Asn Gly Pro Trp Gly Glu Asp Asp Met Arg Cys His
1               5                   10                  15

Asn His Cys Lys Ser Ile Arg Gly Tyr Lys Gly Gly Tyr Cys Ala Lys
            20                  25                  30

Gly Gly Phe Val Cys Lys Cys Tyr
        35                  40

<210> SEQ ID NO 80
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 80

Gly Phe Gly Cys Asn Gly Pro Trp Asp Gly Asp Asp Met Arg Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 81
<211> LENGTH: 40
<212> TYPE: PRT
<213> ORGANISM: Artificial
<220> FEATURE:
```

<223> OTHER INFORMATION: Synthetic antimicrobial polypeptide

<400> SEQUENCE: 81

Gly Phe Gly Cys Asn Gly Pro Trp Asp Glu Gly Asp Met Gln Cys His
1               5                   10                  15

Asn His Cys Lys Ser Ile Lys Gly Tyr Lys Gly Gly Tyr Cys Ala Arg
            20                  25                  30

Gly Gly Phe Val Cys Lys Cys Tyr
        35                  40

<210> SEQ ID NO 82
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 82

Gly Phe Gly Cys Asn Gly Pro Trp Asp Glu Gly Asp Met Gln Cys His
1               5                   10                  15

Ser His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 83
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 83

Gly Phe Gly Cys Asn Gly Pro Trp Asp Glu Gly Asp Met Gln Cys His
1               5                   10                  15

Asn His Cys Lys Ser Val Lys Gly Tyr Lys Gly Gly Tyr Cys Ala Lys
            20                  25                  30

Gly Gly Phe Val Cys Lys Cys Tyr
        35                  40

<210> SEQ ID NO 84
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 84

Gly Phe Gly Cys Asn Gly Pro Trp Asp Glu Asn Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Ile Cys Lys Cys Tyr
        35                  40

<210> SEQ ID NO 85
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 85

```
Gly Phe Gly Cys Asn Gly Pro Trp Asp Glu Arg Asp Ile Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 86
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 86

```
Gly Phe Gly Cys Asn Gly Pro Trp Asp Glu Asp Asp Met Val Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40
```

<210> SEQ ID NO 87
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 87

```
Gly Phe Gly Cys Asn Gly Pro Trp Asp Glu Asp Asp Met Arg Cys His
1               5                   10                  15

Asn His Cys Lys Ser Ile Lys Gly Tyr Arg Gly Gly Tyr Cys Ala Lys
            20                  25                  30

Gly Gly Phe Val Cys Arg Cys Tyr
        35                  40
```

<210> SEQ ID NO 88
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 88

```
Gly Phe Gly Cys Lys Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 89
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 89

```
Gly Phe Gly Cys Tyr Gly Pro Trp Asp Glu Asp Asp Met Gln Cys His
1               5                   10                  15
```

```
Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 90
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 90

Gly Phe Gly Cys Asn Gly Pro Trp Asp Glu Asp Asp Lys Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 91
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 91

Gly Phe Gly Cys Asn Gly Pro Trp Asp Glu Asp Asp Met Leu Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 92
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 92

Gly Phe Gly Cys Asn Gly Pro Trp Asp Glu Asp Asp Met Arg Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 93
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 93

Gly Phe Gly Cys Asn Gly Pro Trp Asp Glu Asp Asp Met Gln Cys His
1               5                   10                  15

His His Cys Lys Ser Ile Lys Gly Tyr Lys Gly Gly Tyr Cys Ala Lys
            20                  25                  30
```

```
Gly Gly Phe Val Cys Lys Cys Tyr
        35                  40

<210> SEQ ID NO 94
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 94

Gly Phe Gly Cys Asn Gly Pro Trp Asp Glu Asp Asp Met Gln Cys His
1               5                   10                  15

Ile His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 95
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 95

Gly Phe Gly Cys Asn Gly Pro Trp Asp Glu Asp Asp Met Gln Cys His
1               5                   10                  15

Arg His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 96
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 96

Gly Phe Gly Cys Asn Gly Pro Trp Asp Glu Asp Asp Met Gln Cys His
1               5                   10                  15

Tyr His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 97
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 97

Gly Phe Gly Cys Asn Gly Pro Trp Asp Glu Asp Asp Met Gln Cys His
1               5                   10                  15

Asn His Cys Arg Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 98
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 98

Gly Phe Gly Cys Asn Gly Pro Trp Asp Glu Asp Asp Met Gln Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 99
<211> LENGTH: 41
<212> TYPE: PRT
<213> ORGANISM: Artificial
<220> FEATURE:
<223> OTHER INFORMATION: Synthetic antimicrobial polypeptide

<400> SEQUENCE: 99

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr Arg
        35                  40

<210> SEQ ID NO 100
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 100

Gly Phe Gly Cys Tyr Gly Pro Trp Asp Glu Asp Asp Met Leu Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 101
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 101

Gly Phe Gly Cys Asn Gly Pro Trp Asp Glu Gly Asp Met Gln Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 102

-continued

```
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 102

Gly Phe Gly Cys Asn Gly Pro Trp Asp Glu Gly Asp Lys Gln Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 103
<211> LENGTH: 41
<212> TYPE: PRT
<213> ORGANISM: Artificial
<220> FEATURE:
<223> OTHER INFORMATION: Synthetic antimicrobial polypeptide

<400> SEQUENCE: 103

Gly Phe Gly Cys Asn Gly Pro Trp Asp Glu Asp Asp Lys Gln Cys His
1               5                   10                  15

Arg His Cys Lys Ser Ile Lys Gly Tyr Lys Gly Gly Tyr Cys Ala Lys
            20                  25                  30

Gly Gly Phe Val Cys Lys Cys Tyr Arg
        35                  40

<210> SEQ ID NO 104
<211> LENGTH: 41
<212> TYPE: PRT
<213> ORGANISM: Artificial
<220> FEATURE:
<223> OTHER INFORMATION: Synthetic antimicrobial polypeptide

<400> SEQUENCE: 104

Gly Phe Gly Cys Asn Gly Pro Trp Asp Glu Asp Asp Met Gln Cys His
1               5                   10                  15

Arg His Cys Lys Ser Ile Lys Gly Tyr Lys Gly Gly Tyr Cys Ala Lys
            20                  25                  30

Gly Gly Phe Val Cys Lys Cys Tyr Arg
        35                  40

<210> SEQ ID NO 105
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 105

Gly Phe Gly Cys Asn Gly Pro Trp Asp Glu Asn Asp Met Gln Cys His
1               5                   10                  15

Asn His Cys Lys Phe Ile Lys Gly Tyr Lys Gly Gly Tyr Cys Ala Lys
            20                  25                  30

Gly Gly Phe Val Cys Lys Cys Tyr
        35                  40

<210> SEQ ID NO 106
<211> LENGTH: 40
<212> TYPE: PRT
<213> ORGANISM: Artificial
```

```
<220> FEATURE:
<223> OTHER INFORMATION: Synthetic antimicrobial polypeptide

<400> SEQUENCE: 106

Gly Phe Gly Cys Asn Gly Pro Trp Asp Glu Asp Asp Lys Gln Cys His
1               5                   10                  15

Arg His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 107
<211> LENGTH: 41
<212> TYPE: PRT
<213> ORGANISM: Artificial
<220> FEATURE:
<223> OTHER INFORMATION: Synthetic antimicrobial polypeptide

<400> SEQUENCE: 107

Gly Phe Gly Cys Asn Gly Pro Trp Asp Glu Asp Asp Lys Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr Arg
        35                  40

<210> SEQ ID NO 108
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 108

Gly Phe Gly Cys Asn Gly Pro Trp Asp Glu Asp Asp Lys Gln Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 109
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 109

Gly Phe Gly Cys Asn Gly Pro Trp Asp Glu Asp Asp Lys Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Arg Cys Tyr
        35                  40

<210> SEQ ID NO 110
<211> LENGTH: 41
<212> TYPE: PRT
<213> ORGANISM: Artificial
<220> FEATURE:
<223> OTHER INFORMATION: Synthetic antimicrobial polypeptide
```

-continued

```
<400> SEQUENCE: 110

Gly Phe Gly Cys Asn Gly Pro Trp Asp Glu Gly Asp Met Gln Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr Arg
        35                  40

<210> SEQ ID NO 111
<211> LENGTH: 41
<212> TYPE: PRT
<213> ORGANISM: Artificial
<220> FEATURE:
<223> OTHER INFORMATION: Synthetic antimicrobial polypeptide

<400> SEQUENCE: 111

Gly Phe Gly Cys Asn Gly Pro Trp Asp Glu Gly Asp Lys Gln Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr Arg
        35                  40

<210> SEQ ID NO 112
<211> LENGTH: 41
<212> TYPE: PRT
<213> ORGANISM: Artificial
<220> FEATURE:
<223> OTHER INFORMATION: Synthetic antimicrobial polypeptide

<400> SEQUENCE: 112

Gly Phe Gly Cys Asn Gly Pro Trp Asp Glu Asp Met Arg Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr Arg
        35                  40

<210> SEQ ID NO 113
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 113

Gly Phe Gly Cys Asn Gly Pro Trp Asp Glu Asp Met Arg Cys His
1               5                   10                  15

Asn His Cys Lys Ser Ile Lys Gly Tyr Lys Gly Gly Tyr Cys Ala Lys
            20                  25                  30

Gly Gly Phe Ile Cys Lys Cys Tyr
        35                  40

<210> SEQ ID NO 114
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 114

Gly Phe Gly Cys Asn Gly Pro Trp Asp Glu Asp Asp Met Arg Cys His
```

```
                1               5                  10                 15
Asn His Cys Lys Ser Ile Lys Gly Tyr Arg Gly Gly Tyr Cys Ala Lys
            20                  25                 30

Gly Gly Phe Val Cys Lys Cys Tyr
        35                  40
```

<210> SEQ ID NO 115
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 115

```
Gly Phe Gly Cys Asn Gly Pro Trp Asp Glu Asp Asp Met Gln Cys His
1               5                   10                  15

Asn His Cys Lys Phe Ile Lys Gly Tyr Lys Gly Gly Tyr Cys Thr Lys
            20                  25                  30

Gly Gly Phe Val Cys Lys Cys Tyr
        35                  40
```

<210> SEQ ID NO 116
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 116

```
Gly Phe Gly Cys Asn Gly Pro Trp Asp Glu Asp Asp Met Lys Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40
```

<210> SEQ ID NO 117
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 117

```
Gly Phe Gly Cys Asn Gly Pro Trp Asp Glu Asp Asp Met Gln Cys His
1               5                   10                  15

Asn His Cys Lys Ser Ile Lys Gly Arg Lys Gly Gly Tyr Cys Ala Lys
            20                  25                  30

Gly Gly Phe Val Cys Lys Cys Tyr
        35                  40
```

<210> SEQ ID NO 118
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 118

```
Gly Leu Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
```

```
                20                  25                  30

Gly Gly Phe Val Cys Lys Cys Tyr
        35                  40

<210> SEQ ID NO 119
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 119

Gly Trp Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 120
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 120

Gly Ile Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 121
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 121

Gly Phe Gly Cys Leu Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 122
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 122

Gly Phe Gly Cys Met Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
```

<210> SEQ ID NO 123
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 123

Gly Phe Gly Cys Asn Arg Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 124
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 124

Gly Phe Gly Cys Asn Ala Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 125
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 125

Gly Phe Gly Cys Asn Lys Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 126
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 126

Gly Phe Gly Cys Asn Gly Ala Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 127
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 127

Gly Phe Gly Cys Asn Gly Leu Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 128
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 128

Gly Phe Gly Cys Asn Gly Val Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 129
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 129

Gly Phe Gly Cys Asn Gly Pro Trp Cys Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 130
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 130

Gly Phe Gly Cys Asn Gly Pro Trp Ile Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 131
<211> LENGTH: 40
<212> TYPE: PRT

<213> ORGANISM: Artificial
<220> FEATURE:
<223> OTHER INFORMATION: Synthetic antimicrobial polypeptide

<400> SEQUENCE: 131

Gly Phe Gly Cys Asn Gly Pro Trp Arg Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 132
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 132

Gly Phe Gly Cys Asn Gly Pro Trp Trp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 133
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 133

Gly Phe Gly Cys Asn Gly Pro Trp Asp Ala Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 134
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 134

Gly Phe Gly Cys Asn Gly Pro Trp Asp Leu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 135
<211> LENGTH: 40
<212> TYPE: PRT
<213> ORGANISM: Artificial
<220> FEATURE:
<223> OTHER INFORMATION: Synthetic antimicrobial polypeptide -continued

<400> SEQUENCE: 135

Gly Phe Gly Cys Asn Gly Pro Trp Asp Cys Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 136
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 136

Gly Phe Gly Cys Asn Gly Pro Trp Asp Gln Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 137
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 137

Gly Phe Gly Cys Asn Gly Pro Trp Asp Glu Ala Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 138
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 138

Gly Phe Gly Cys Asn Gly Pro Trp Asp Glu Cys Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 139
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 139

```
Gly Phe Gly Cys Asn Gly Pro Trp Asp Glu Asp Pro Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 140
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 140

Gly Phe Gly Cys Asn Gly Pro Trp Asp Glu Asp Ala Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 141
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 141

Gly Phe Gly Cys Asn Gly Pro Trp Asp Glu Asp Phe Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 142
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 142

Gly Phe Gly Cys Asn Gly Pro Trp Asp Glu Asp Gly Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 143
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 143

Gly Phe Gly Cys Asn Gly Pro Trp Asp Glu Asp Leu Gln Cys His
1               5                   10                  15
```

Asn His Cys Lys Ser Ile Lys Gly Tyr Lys Gly Gly Tyr Cys Ala Lys
            20                  25                  30

Gly Gly Phe Val Cys Lys Cys Tyr
            35                  40

<210> SEQ ID NO 144
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 144

Gly Phe Gly Cys Asn Gly Pro Trp Asp Glu Asp Thr Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
            35                  40

<210> SEQ ID NO 145
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 145

Gly Phe Gly Cys Asn Gly Pro Trp Asp Glu Asp Tyr Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
            35                  40

<210> SEQ ID NO 146
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 146

Gly Phe Gly Cys Asn Gly Pro Trp Asp Glu Asp Met Ala Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
            35                  40

<210> SEQ ID NO 147
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 147

Gly Phe Gly Cys Asn Gly Pro Trp Asp Glu Asp Met Cys Cys His
1               5                   10                  15

Asn His Cys Lys Ser Ile Lys Gly Tyr Lys Gly Gly Tyr Cys Ala Lys
            20                  25                  30

```
Gly Gly Phe Val Cys Lys Cys Tyr
        35                  40
```

<210> SEQ ID NO 148
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 148

```
Gly Phe Gly Cys Asn Gly Pro Trp Asp Glu Asp Asp Met Ile Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 149
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 149

```
Gly Phe Gly Cys Asn Gly Pro Trp Asp Glu Asp Asp Met Lys Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 150
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 150

```
Gly Phe Gly Cys Asn Gly Pro Trp Asp Glu Asp Asp Met Met Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 151
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 151

```
Gly Phe Gly Cys Asn Gly Pro Trp Asp Glu Asp Asp Met Pro Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 152
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 152

Gly Phe Gly Cys Asn Gly Pro Trp Asp Glu Asp Met Thr Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 153
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 153

Gly Phe Gly Cys Asn Gly Pro Trp Asp Glu Asp Met Val Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 154
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 154

Gly Phe Gly Cys Asn Gly Pro Trp Asp Glu Asp Met Trp Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 155
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 155

Gly Phe Gly Cys Asn Gly Pro Trp Asp Glu Asp Met Gln Cys His
1               5                   10                  15

Asn Ala Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 156
<211> LENGTH: 40

```
<212> TYPE: PRT
<213> ORGANISM: Artificial
<220> FEATURE:
<223> OTHER INFORMATION: Synthetic antimicrobial polypeptide

<400> SEQUENCE: 156

Gly Phe Gly Cys Asn Gly Pro Trp Asp Glu Asp Asp Met Gln Cys His
1               5                   10                  15

Asn Phe Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 157
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 157

Gly Phe Gly Cys Asn Gly Pro Trp Asp Glu Asp Asp Met Gln Cys His
1               5                   10                  15

Asn Gln Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 158
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 158

Gly Phe Gly Cys Asn Gly Pro Trp Asp Glu Asp Asp Met Gln Cys His
1               5                   10                  15

Asn Thr Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 159
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 159

Gly Phe Gly Cys Asn Gly Pro Trp Asp Glu Asp Asp Met Gln Cys His
1               5                   10                  15

Asn Val Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 160
<211> LENGTH: 40
<212> TYPE: PRT
<213> ORGANISM: Artificial
<220> FEATURE:
```

-continued

<223> OTHER INFORMATION: Synthetic antimicrobial polypeptide

<400> SEQUENCE: 160

Gly Phe Gly Cys Asn Gly Pro Trp Asp Glu Asp Asp Met Gln Cys His
1               5                   10                  15

Asn His Cys Gln Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 161
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 161

Gly Phe Gly Cys Asn Gly Pro Trp Asp Glu Asp Asp Met Gln Cys His
1               5                   10                  15

Asn His Cys Lys Ser Met Lys Gly Tyr Lys Gly Gly Tyr Cys Ala Lys
            20                  25                  30

Gly Gly Phe Val Cys Lys Cys Tyr
        35                  40

<210> SEQ ID NO 162
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 162

Gly Phe Gly Cys Asn Gly Pro Trp Asp Glu Asp Asp Met Gln Cys His
1               5                   10                  15

Asn His Cys Lys Ser Thr Lys Gly Tyr Lys Gly Gly Tyr Cys Ala Lys
            20                  25                  30

Gly Gly Phe Val Cys Lys Cys Tyr
        35                  40

<210> SEQ ID NO 163
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 163

Gly Phe Gly Cys Asn Gly Pro Trp Asp Glu Asp Asp Met Gln Cys His
1               5                   10                  15

Asn His Cys Lys Ser Trp Lys Gly Tyr Lys Gly Gly Tyr Cys Ala Lys
            20                  25                  30

Gly Gly Phe Val Cys Lys Cys Tyr
        35                  40

<210> SEQ ID NO 164
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 164

```
Gly Phe Gly Cys Asn Gly Pro Trp Asp Glu Asp Met Gln Cys His
1               5                   10                  15

Asn His Cys Lys Ser Ile Lys Ala Tyr Lys Gly Gly Tyr Cys Ala Lys
            20                  25                  30

Gly Gly Phe Val Cys Lys Cys Tyr
        35                  40
```

<210> SEQ ID NO 165
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 165

```
Gly Phe Gly Cys Asn Gly Pro Trp Asp Glu Asp Met Gln Cys His
1               5                   10                  15

Asn His Cys Lys Ser Ile Lys Pro Tyr Lys Gly Gly Tyr Cys Ala Lys
            20                  25                  30

Gly Gly Phe Val Cys Lys Cys Tyr
        35                  40
```

<210> SEQ ID NO 166
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 166

```
Gly Phe Gly Cys Asn Gly Pro Trp Asp Glu Asp Met Gln Cys His
1               5                   10                  15

Asn His Cys Lys Ser Ile Lys Phe Tyr Lys Gly Gly Tyr Cys Ala Lys
            20                  25                  30

Gly Gly Phe Val Cys Lys Cys Tyr
        35                  40
```

<210> SEQ ID NO 167
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 167

```
Gly Phe Gly Cys Asn Gly Pro Trp Asp Glu Asp Met Gln Cys His
1               5                   10                  15

Asn His Cys Lys Ser Ile Lys Ile Tyr Lys Gly Gly Tyr Cys Ala Lys
            20                  25                  30

Gly Gly Phe Val Cys Lys Cys Tyr
        35                  40
```

<210> SEQ ID NO 168
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 168

```
Gly Phe Gly Cys Asn Gly Pro Trp Asp Glu Asp Met Gln Cys His
1               5                   10                  15
```

```
Asn His Cys Lys Ser Ile Lys Gln Tyr Lys Gly Gly Tyr Cys Ala Lys
            20                  25                  30

Gly Gly Phe Val Cys Lys Cys Tyr
        35                  40

<210> SEQ ID NO 169
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 169

Gly Phe Gly Cys Asn Gly Pro Trp Asp Glu Asp Asp Met Gln Cys His
1               5                   10                  15

Asn His Cys Lys Ser Ile Lys Arg Tyr Lys Gly Gly Tyr Cys Ala Lys
            20                  25                  30

Gly Gly Phe Val Cys Lys Cys Tyr
        35                  40

<210> SEQ ID NO 170
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 170

Gly Phe Gly Cys Asn Gly Pro Trp Asp Glu Asp Asp Met Gln Cys His
1               5                   10                  15

Asn His Cys Lys Ser Ile Lys Ser Tyr Lys Gly Gly Tyr Cys Ala Lys
            20                  25                  30

Gly Gly Phe Val Cys Lys Cys Tyr
        35                  40

<210> SEQ ID NO 171
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 171

Gly Phe Gly Cys Asn Gly Pro Trp Asp Glu Asp Asp Met Gln Cys His
1               5                   10                  15

Asn His Cys Lys Ser Ile Lys Thr Tyr Lys Gly Gly Tyr Cys Ala Lys
            20                  25                  30

Gly Gly Phe Val Cys Lys Cys Tyr
        35                  40

<210> SEQ ID NO 172
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 172

Gly Phe Gly Cys Asn Gly Pro Trp Asp Glu Asp Asp Met Gln Cys His
1               5                   10                  15

Asn His Cys Lys Ser Ile Lys Tyr Tyr Lys Gly Gly Tyr Cys Ala Lys
            20                  25                  30
```

```
Gly Gly Phe Val Cys Lys Cys Tyr
        35                  40

<210> SEQ ID NO 173
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 173

Gly Phe Gly Cys Asn Gly Pro Trp Asp Glu Asp Asp Met Gln Cys His
1               5                   10                  15

Asn His Cys Lys Ser Ile Lys Gly His Lys Gly Gly Tyr Cys Ala Lys
            20                  25                  30

Gly Gly Phe Val Cys Lys Cys Tyr
        35                  40

<210> SEQ ID NO 174
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 174

Gly Phe Gly Cys Asn Gly Pro Trp Asp Glu Asp Asp Met Gln Cys His
1               5                   10                  15

Asn His Cys Lys Ser Ile Lys Gly Lys Lys Gly Gly Tyr Cys Ala Lys
            20                  25                  30

Gly Gly Phe Val Cys Lys Cys Tyr
        35                  40

<210> SEQ ID NO 175
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 175

Gly Phe Gly Cys Asn Gly Pro Trp Asp Glu Asp Asp Met Gln Cys His
1               5                   10                  15

Asn His Cys Lys Ser Ile Lys Gly Leu Lys Gly Gly Tyr Cys Ala Lys
            20                  25                  30

Gly Gly Phe Val Cys Lys Cys Tyr
        35                  40

<210> SEQ ID NO 176
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 176

Gly Phe Gly Cys Asn Gly Pro Trp Asp Glu Asp Asp Met Gln Cys His
1               5                   10                  15

Asn His Cys Lys Ser Ile Lys Gly Met Lys Gly Gly Tyr Cys Ala Lys
            20                  25                  30

Gly Gly Phe Val Cys Lys Cys Tyr
        35                  40
```

<210> SEQ ID NO 177
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 177

Gly Phe Gly Cys Asn Gly Pro Trp Asp Glu Asp Asp Met Gln Cys His
1               5                   10                  15

Asn His Cys Lys Ser Ile Lys Gly Asn Lys Gly Gly Tyr Cys Ala Lys
            20                  25                  30

Gly Gly Phe Val Cys Lys Cys Tyr
        35                  40

<210> SEQ ID NO 178
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 178

Gly Phe Gly Cys Asn Gly Pro Trp Asp Glu Asp Asp Met Gln Cys His
1               5                   10                  15

Asn His Cys Lys Ser Ile Lys Gly Gln Lys Gly Gly Tyr Cys Ala Lys
            20                  25                  30

Gly Gly Phe Val Cys Lys Cys Tyr
        35                  40

<210> SEQ ID NO 179
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 179

Gly Phe Gly Cys Asn Gly Pro Trp Asp Glu Asp Asp Met Gln Cys His
1               5                   10                  15

Asn His Cys Lys Ser Ile Lys Gly Ser Lys Gly Gly Tyr Cys Ala Lys
            20                  25                  30

Gly Gly Phe Val Cys Lys Cys Tyr
        35                  40

<210> SEQ ID NO 180
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 180

Gly Phe Gly Cys Asn Gly Pro Trp Asp Glu Asp Asp Met Gln Cys His
1               5                   10                  15

Asn His Cys Lys Ser Ile Lys Gly Val Lys Gly Gly Tyr Cys Ala Lys
            20                  25                  30

Gly Gly Phe Val Cys Lys Cys Tyr
        35                  40

<210> SEQ ID NO 181

<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 181

Gly Phe Gly Cys Asn Gly Pro Trp Asp Glu Asp Asp Met Gln Cys His
1               5                   10                  15

Asn His Cys Lys Ser Ile Lys Gly Tyr Phe Gly Gly Tyr Cys Ala Lys
            20                  25                  30

Gly Gly Phe Val Cys Lys Cys Tyr
        35                  40

<210> SEQ ID NO 182
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 182

Gly Phe Gly Cys Asn Gly Pro Trp Asp Glu Asp Asp Met Gln Cys His
1               5                   10                  15

Asn His Cys Lys Ser Ile Lys Gly Tyr His Gly Gly Tyr Cys Ala Lys
            20                  25                  30

Gly Gly Phe Val Cys Lys Cys Tyr
        35                  40

<210> SEQ ID NO 183
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 183

Gly Phe Gly Cys Asn Gly Pro Trp Asp Glu Asp Asp Met Gln Cys His
1               5                   10                  15

Asn His Cys Lys Ser Ile Lys Gly Tyr Thr Gly Gly Tyr Cys Ala Lys
            20                  25                  30

Gly Gly Phe Val Cys Lys Cys Tyr
        35                  40

<210> SEQ ID NO 184
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 184

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Ala Cys Ala Lys
            20                  25                  30

Gly Gly Phe Val Cys Lys Cys Tyr
        35                  40

<210> SEQ ID NO 185
<211> LENGTH: 40
<212> TYPE: PRT
<213> ORGANISM: Artificial

```
<220> FEATURE:
<223> OTHER INFORMATION: Synthetic antimicrobial polypeptide

<400> SEQUENCE: 185

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly His Cys Ala Lys
            20                  25                  30

Gly Gly Phe Val Cys Lys Cys Tyr
        35                  40

<210> SEQ ID NO 186
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 186

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Leu Cys Ala Lys
            20                  25                  30

Gly Gly Phe Val Cys Lys Cys Tyr
        35                  40

<210> SEQ ID NO 187
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 187

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Met Cys Ala Lys
            20                  25                  30

Gly Gly Phe Val Cys Lys Cys Tyr
        35                  40

<210> SEQ ID NO 188
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 188

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Ser Cys Ala Lys
            20                  25                  30

Gly Gly Phe Val Cys Lys Cys Tyr
        35                  40

<210> SEQ ID NO 189
<211> LENGTH: 40
<212> TYPE: PRT
<213> ORGANISM: Artificial
<220> FEATURE:
<223> OTHER INFORMATION: Synthetic antimicrobial polypeptide
```

```
<400> SEQUENCE: 189

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Glu Lys
            20                  25                  30

Gly Gly Phe Val Cys Lys Cys Tyr
        35                  40

<210> SEQ ID NO 190
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 190

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys His Lys
            20                  25                  30

Gly Gly Phe Val Cys Lys Cys Tyr
        35                  40

<210> SEQ ID NO 191
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 191

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ile Lys
            20                  25                  30

Gly Gly Phe Val Cys Lys Cys Tyr
        35                  40

<210> SEQ ID NO 192
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 192

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Arg Lys
            20                  25                  30

Gly Gly Phe Val Cys Lys Cys Tyr
        35                  40

<210> SEQ ID NO 193
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 193

Gly Phe Gly Cys Asn Gly Pro Trp Asp Glu Asp Asp Met Gln Cys His
```

```
                1               5                  10                  15
Asn His Cys Lys Ser Ile Lys Gly Tyr Lys Gly Gly Tyr Cys Ser Lys
                20                  25                  30

Gly Gly Phe Val Cys Lys Cys Tyr
        35                  40

<210> SEQ ID NO 194
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 194

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Val Lys
                20                  25                  30

Gly Gly Phe Val Cys Lys Cys Tyr
        35                  40

<210> SEQ ID NO 195
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 195

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Arg
                20                  25                  30

Gly Gly Phe Val Cys Lys Cys Tyr
        35                  40

<210> SEQ ID NO 196
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 196

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Thr
                20                  25                  30

Gly Gly Phe Val Cys Lys Cys Tyr
        35                  40

<210> SEQ ID NO 197
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 197

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
```

Glu Gly Phe Val Cys Lys Cys Tyr
        35                  40

<210> SEQ ID NO 198
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 198

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Asn Gly Phe Val Cys Lys Cys Tyr
        35                  40

<210> SEQ ID NO 199
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 199

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Ser Gly Phe Val Cys Lys Cys Tyr
        35                  40

<210> SEQ ID NO 200
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 200

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Thr Gly Phe Val Cys Lys Cys Tyr
        35                  40

<210> SEQ ID NO 201
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 201

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly His Phe Val Cys Lys Cys Tyr

```
                35                  40

<210> SEQ ID NO 202
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 202

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Trp Phe Val Cys Lys Cys Tyr
        35                  40

<210> SEQ ID NO 203
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 203

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Ala Val Cys Lys Cys Tyr
        35                  40

<210> SEQ ID NO 204
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 204

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly His Val Cys Lys Cys Tyr
        35                  40

<210> SEQ ID NO 205
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 205

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Ile Val Cys Lys Cys Tyr
        35                  40
```

<210> SEQ ID NO 206
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 206

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Met Val Cys Lys Cys Tyr
        35                  40

<210> SEQ ID NO 207
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 207

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Val Val Cys Lys Cys Tyr
        35                  40

<210> SEQ ID NO 208
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 208

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Trp Val Cys Lys Cys Tyr
        35                  40

<210> SEQ ID NO 209
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 209

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Ile Cys Lys Cys Tyr
        35                  40

<210> SEQ ID NO 210
<211> LENGTH: 40
<212> TYPE: PRT

<213> ORGANISM: Artificial
<220> FEATURE:
<223> OTHER INFORMATION: Synthetic antimicrobial polypeptide

<400> SEQUENCE: 210

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Lys Cys Lys Cys Tyr
        35                  40

<210> SEQ ID NO 211
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 211

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Gln Cys Lys Cys Tyr
        35                  40

<210> SEQ ID NO 212
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 212

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Arg Cys Lys Cys Tyr
        35                  40

<210> SEQ ID NO 213
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 213

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys His Cys Tyr
        35                  40

<210> SEQ ID NO 214
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 214

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Asn Cys Tyr
        35                  40

<210> SEQ ID NO 215
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 215

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Arg Cys Tyr
        35                  40

<210> SEQ ID NO 216
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 216

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Ile
        35                  40

<210> SEQ ID NO 217
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 217

Gly Phe Gly Cys Asn Gly Pro Trp Leu Glu Asp Asp Met Gln Cys His
1               5                   10                  15

Asn His Cys Lys Ser Ile Lys Gly Tyr Asn Gly Gly Tyr Cys Ala Lys
            20                  25                  30

Gly Gly Phe Val Cys Lys Cys Tyr
        35                  40

<210> SEQ ID NO 218
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 218

Gly Phe Gly Cys Asn Gly Pro Trp Asp Glu Leu Asp Ile Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 219
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 219

Gly Phe Gly Cys Asn Gly Pro Trp Asp Glu Asp Asp Arg Gln Cys His
1               5                   10                  15

Asn His Cys Lys Ser Ile Lys Gly Tyr Lys Gly Gly Phe Cys Ala Lys
            20                  25                  30

Gly Gly Phe Val Cys Lys Cys Tyr
        35                  40

<210> SEQ ID NO 220
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 220

Gly Phe Gly Cys Asn Gly Pro Trp Asp Glu Asp Asp Met Arg Cys His
1               5                   10                  15

Asn His Cys Lys Ser Ile Arg Gly Tyr Arg Gly Gly Tyr Cys Ala Lys
            20                  25                  30

Gly Gly Phe Val Cys Lys Cys Tyr
        35                  40

<210> SEQ ID NO 221
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 221

Gly Phe Gly Cys Asn Gly Pro Trp Asp Glu Asp Asp Met Arg Cys His
1               5                   10                  15

Asn His Cys Arg Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 222
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 222

Gly Phe Gly Cys Asn Gly Pro Trp Asp Glu Asp Asp Met Ser Cys His
1               5                   10                  15

Asn His Cys Lys Ser Ile Lys Gly Tyr Lys Gly Gly Tyr Cys Ala Lys
            20                  25                  30

Gly Gly Phe Val Cys Arg Cys Tyr
        35                  40

<210> SEQ ID NO 223
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 223

Gly Phe Gly Cys Asn Gly Pro Trp Asp Glu Asp Asp Met Gln Cys His
1               5                   10                  15

Ser His Cys Lys Ser Ile Arg Gly Tyr Lys Gly Gly Tyr Cys Ala Lys
            20                  25                  30

Gly Gly Phe Val Cys Lys Cys Tyr
        35                  40

<210> SEQ ID NO 224
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 224

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Phe Cys Ala Arg
            20                  25                  30

Gly Gly Phe Val Cys Lys Cys Tyr
        35                  40

<210> SEQ ID NO 225
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 225

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Arg
            20                  25                  30

Gly Lys Phe Val Cys Lys Cys Tyr
        35                  40

<210> SEQ ID NO 226
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 226

Gly Phe Gly Cys Arg Gly Pro Trp Asp Glu Asp Asp Tyr Gln Cys His
1               5                   10                  15

Arg His Cys Lys Ser Ile Lys Gly Tyr Lys Gly Gly Tyr Cys Ala Lys
            20                  25                  30

```
Gly Gly Phe Val Cys Lys Cys Tyr
        35                  40

<210> SEQ ID NO 227
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 227

Gly Phe Gly Cys Asn Gly Pro Trp Ser Glu Asp Met Lys Cys His
1               5                   10                  15

Asn His Cys Lys Ser Ile Lys Gly Tyr Lys Gly Gly Tyr Cys Ala Lys
            20                  25                  30

Gly Gly Phe Leu Cys Lys Cys Tyr
        35                  40

<210> SEQ ID NO 228
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 228

Gly Phe Gly Cys Ser Gly Pro Trp Asp Glu Asp Trp Gln Cys His
1               5                   10                  15

Arg His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 229
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 229

Gly Phe Gly Cys Asn Gly Pro Trp Asp Glu Asp Gly Gln Cys His
1               5                   10                  15

Arg His Cys Lys Ser Ile Lys Gly Tyr Lys Gly Gly Tyr Cys Ala Lys
            20                  25                  30

Ala Gly Phe Val Cys Lys Cys Tyr
        35                  40

<210> SEQ ID NO 230
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 230

Gly Phe Gly Cys Ser Gly Pro Trp Ser Glu Asp Leu Arg Cys His
1               5                   10                  15

Val His Cys Lys Ser Ile Lys Gly Tyr Lys Gly Gly Tyr Cys Ser Lys
            20                  25                  30

Gly Gly Phe Val Cys Lys Cys Tyr
        35                  40
```

<210> SEQ ID NO 231
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 231

Gly Phe Gly Cys Asn Gly Pro Trp Ser Glu Asp Asp Met Leu Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 232
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 232

Gly Phe Gly Cys Ser Gly Pro Trp Ala Glu Asp Asp Met Gln Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 233
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 233

Gly Phe Gly Cys Gly Gly Pro Trp Asp Glu Asp Asp Leu Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 234
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 234

Gly Phe Gly Cys Asn Gly Pro Trp Ala Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Arg Cys Tyr
        35                  40

<210> SEQ ID NO 235
<211> LENGTH: 40

<212> TYPE: PRT
<213> ORGANISM: Artificial
<220> FEATURE:
<223> OTHER INFORMATION: Synthetic antimicrobial polypeptide

<400> SEQUENCE: 235

Gly Phe Gly Cys Arg Gly Pro Trp Asp Glu Asp Val Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 236
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 236

Gly Phe Gly Cys Gly Gly Pro Trp Asp Glu Asp Tyr Gln Cys His
1               5                   10                  15

Lys His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 237
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 237

Gly Phe Gly Cys Asn Gly Pro Trp Asp Glu Asp Phe Lys Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 238
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 238

Gly Phe Gly Cys Ala Gly Pro Trp Ser Glu Asp Leu Gln Cys His
1               5                   10                  15

Thr His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 239
<211> LENGTH: 40
<212> TYPE: PRT
<213> ORGANISM: Artificial
<220> FEATURE:

<223> OTHER INFORMATION: Synthetic antimicrobial polypeptide

<400> SEQUENCE: 239

Gly Phe Gly Cys Asn Gly Pro Trp Asp Glu Asp Asp Thr Lys Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 240
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 240

Gly Phe Gly Cys Asn Gly Pro Trp Asp Glu Asp Asp Leu Lys Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 241
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 241

Gly Phe Gly Cys Asn Gly Pro Trp Asn Glu Asp Asp Leu Arg Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 242
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 242

Gly Phe Gly Cys Asn Gly Pro Trp Ala Glu Asp Asp Met His Cys His
1               5                   10                  15

Asn His Cys Lys Ser Ile Lys Gly Tyr Arg Gly Gly Tyr Cys Ala Lys
            20                  25                  30

Gly Gly Phe Leu Cys Lys Cys Tyr
        35                  40

<210> SEQ ID NO 243
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 243

```
Gly Phe Gly Cys Ser Gly Pro Trp Ser Glu Asp Val Gln Cys His
1               5                   10                  15

Arg His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 244
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 244

```
Gly Phe Gly Cys Gly Gly Pro Trp Ser Glu Asp Leu Gln Cys His
1               5                   10                  15

Gln His Cys Lys Ser Ile Lys Gly Tyr Lys Gly Tyr Cys Thr Lys
            20                  25                  30

Gly Gly Phe Val Cys Lys Cys Tyr
        35                  40
```

<210> SEQ ID NO 245
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 245

```
Gly Phe Gly Cys Asn Gly Pro Trp Asp Glu Asp Val Gln Cys His
1               5                   10                  15

Thr His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 246
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 246

```
Gly Phe Gly Cys Asn Gly Pro Trp Ser Glu Asp Leu His Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

<210> SEQ ID NO 247
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 247

```
Gly Phe Gly Cys Asn Gly Pro Trp Ser Glu Asp Met Leu Cys His
1               5                   10                  15
```

```
Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 248
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 248

Gly Phe Gly Cys Asn Gly Pro Trp Asn Glu Asp Asp Met His Cys His
1               5                   10                  15

Asn His Cys Lys Ser Ile Lys Gly Tyr Lys Gly Gly Tyr Cys Ala Lys
            20                  25                  30

Gly Gly Phe Val Cys Arg Cys Tyr
        35                  40

<210> SEQ ID NO 249
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 249

Gly Phe Gly Cys Asn Gly Pro Trp Asp Glu Asp Tyr Lys Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 250
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 250

Gly Phe Gly Cys Ser Gly Pro Trp Ser Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 251
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 251

Gly Phe Gly Cys Gly Gly Pro Trp Asp Glu Asp Asp Met Lys Cys His
1               5                   10                  15

Asn His Cys Lys Ser Ile Lys Gly Tyr Lys Gly Gly Tyr Cys Ala Lys
            20                  25                  30
```

Gly Gly Phe Val Cys Lys Cys Tyr
        35                  40

<210> SEQ ID NO 252
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 252

Gly Phe Gly Cys Asn Gly Pro Trp Asp Glu Asp Asp Arg Lys Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 253
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 253

Gly Phe Gly Cys Asn Gly Pro Trp Asp Glu Asp Asp Met Gln Cys His
1               5                   10                  15

Lys His Cys Lys Ser Ile Lys Gly Tyr Lys Gly Gly Tyr Cys Ala Arg
            20                  25                  30

Gly Gly Phe Val Cys Lys Cys Tyr
        35                  40

<210> SEQ ID NO 254
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 254

Gly Phe Gly Cys Gly Gly Pro Trp Asp Glu Asp Trp Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 255
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 255

Gly Phe Gly Cys Asn Gly Pro Trp Asp Glu Asp Asp Ala Lys Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

-continued

<210> SEQ ID NO 256
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 256

Gly Phe Gly Cys Lys Gly Pro Trp Asp Glu Asp Leu Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 257
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 257

Gly Phe Gly Cys Gly Gly Pro Trp Asp Glu Asp Trp Gln Cys His
1               5                   10                  15

Ser His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 258
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 258

Gly Phe Gly Cys Asn Gly Pro Trp Asp Glu Asp Asp Met Gln Cys His
1               5                   10                  15

Lys His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 259
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 259

Gly Phe Gly Cys Asn Gly Pro Trp Asp Glu Asp Asp Met Gln Cys His
1               5                   10                  15

Asn His Cys Lys Asn Ile Lys Gly Tyr Lys Gly Gly Tyr Cys Ala Lys
            20                  25                  30

Gly Gly Phe Val Cys Lys Cys Tyr
        35                  40

<210> SEQ ID NO 260

<211> LENGTH: 43
<212> TYPE: PRT
<213> ORGANISM: Artificial
<220> FEATURE:
<223> OTHER INFORMATION: Synthetic antimicrobial polypeptide

<400> SEQUENCE: 260

Gly Phe Gly Cys Asn Gly Pro Trp Asp Glu Asp Asp Met Gln Cys His
1               5                   10                  15

Asn His Cys Lys Ser Ile Lys Gly Tyr Cys Gly Gly Tyr Cys Ala Lys
            20                  25                  30

Gly Gly Phe Val Cys Lys Cys Tyr Arg Cys Gly
        35                  40

<210> SEQ ID NO 261
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 261

Gly Phe Gly Cys His Gly Pro Trp Asp Glu Asp Glu Gln Cys His
1               5                   10                  15

Glu His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 262
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 262

Gly Phe Gly Cys Asn Gly Pro Trp Asp Glu Asp Asp Met Gln Cys His
1               5                   10                  15

Phe His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 263
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 263

Gly Phe Gly Cys Asn Gly Pro Trp Asp Glu Asp Asp Met Gln Cys His
1               5                   10                  15

Ser His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 264
<211> LENGTH: 40
<212> TYPE: PRT
<213> ORGANISM: Artificial

```
<220> FEATURE:
<223> OTHER INFORMATION: Synthetic antimicrobial polypeptide

<400> SEQUENCE: 264

Gly Phe Gly Cys Gly Gly Pro Trp Ala Glu Asp Asp Met Ser Cys His
1               5                   10                  15

Asn His Cys Lys Ser Ile Thr Gly Tyr Lys Gly Gly Tyr Cys Thr Lys
            20                  25                  30

Gly Gly Phe Val Cys Lys Cys Tyr
        35                  40

<210> SEQ ID NO 265
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 265

Gly Phe Gly Cys Asn Gly Pro Trp Asp Glu Asp Met Gln Cys His
1               5                   10                  15

Ala His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 266
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 266

Gly Phe Gly Cys Asn Gly Pro Trp Asp Glu Asp Ser Lys Cys His
1               5                   10                  15

Asn His Cys Lys Ser Ile Lys Gly Tyr Arg Gly Gly Tyr Cys Ala Lys
            20                  25                  30

Gly Gly Phe Val Cys Lys Cys Tyr
        35                  40

<210> SEQ ID NO 267
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 267

Gly Phe Gly Cys Asn Gly Pro Trp Asp Glu Gly Asp Met Gln Cys His
1               5                   10                  15

Ile His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 268
<211> LENGTH: 40
<212> TYPE: PRT
<213> ORGANISM: Artificial
<220> FEATURE:
<223> OTHER INFORMATION: Synthetic antimicrobial polypeptide
```

```
<400> SEQUENCE: 268

Gly Phe Gly Cys Ser Gly Pro Trp Asp Glu Asp Val Gln Cys His
1               5                   10                  15

Thr His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 269
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 269

Gly Phe Gly Cys Asp Gly Pro Trp Ser Glu Asp Met Arg Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 270
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 270

Gly Phe Gly Cys Asn Gly Pro Trp Asp Glu Asp Met Gln Cys His
1               5                   10                  15

Asn His Cys Lys Ala Ile Lys Gly Tyr Lys Gly Gly Tyr Cys Ala Lys
            20                  25                  30

Gly Gly Phe Val Cys Lys Cys Tyr
        35                  40

<210> SEQ ID NO 271
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 271

Gly Phe Gly Cys Asn Gly Pro Trp Asp Glu Asp Met Gln Cys His
1               5                   10                  15

Arg His Cys Lys Ser Ile Lys Gly Arg Lys Gly Gly Tyr Cys Ala Lys
            20                  25                  30

Gly Gly Phe Val Cys Lys Cys Tyr
        35                  40

<210> SEQ ID NO 272
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 272

Gly Phe Gly Cys Ser Gly Pro Trp Asp Glu Asp Val Gln Cys His
```

-continued

```
                1               5                  10                 15
Ala His Cys Lys Ser Ile Lys Gly Tyr Lys Gly Gly Tyr Cys Ala Lys
                 20                 25                 30

Gly Gly Phe Val Cys Lys Cys Tyr
         35                 40

<210> SEQ ID NO 273
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 273

Gly Phe Gly Cys Asn Gly Pro Trp Asp Glu Asp Asp Met Gln Cys His
1               5                   10                  15

Thr His Cys Lys Ser Ile Lys Gly Tyr Lys Gly Gly Tyr Cys Ala Lys
                 20                 25                 30

Gly Gly Phe Val Cys Lys Cys Tyr
         35                 40

<210> SEQ ID NO 274
<211> LENGTH: 40
<212> TYPE: PRT
<213> ORGANISM: Artificial
<220> FEATURE:
<223> OTHER INFORMATION: Synthetic antimicrobial polypeptide

<400> SEQUENCE: 274

Gly Phe Gly Cys Asn Gly Pro Trp Asp Glu Asp Asp Met Gln Cys His
1               5                   10                  15

Asn His Cys Lys Val Ile Lys Gly Tyr Lys Gly Gly Tyr Cys Ala Lys
                 20                 25                 30

Gly Gly Phe Val Cys Lys Cys Tyr
         35                 40
```